(12) United States Patent
Zhao et al.

(10) Patent No.: US 9,402,690 B2
(45) Date of Patent: *Aug. 2, 2016

(54) EFFICIENT 3-D TELESTRATION FOR LOCAL AND REMOTE ROBOTIC PROCTORING

(71) Applicant: Intuitive Surgical Operations, Inc., Sunnyvale, CA (US)

(72) Inventors: Wenyi Zhao, Mountain View, CA (US); Chenyu Wu, Mountain View, CA (US); David Hirvonen, Brooklyn, NY (US); Christopher J. Hasser, Los Altos, CA (US); Brian E. Miller, Los Gatos, CA (US); Catherine J. Mohr, Mountain View, CA (US); Tao Zhao, Sunnyvale, CA (US); Simon Di Maio, Sunnyvale, CA (US); Brian D. Hoffman, Sunnyvale, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/450,251

(22) Filed: Aug. 3, 2014

(65) Prior Publication Data

US 2015/0025392 A1    Jan. 22, 2015

Related U.S. Application Data

(63) Continuation-in-part of application No. 12/465,020, filed on May 13, 2009, now Pat. No. 8,830,224.

(60) Provisional application No. 61/204,046, filed on Dec. 31, 2008.

(51) Int. Cl.
*G06T 15/00* (2011.01)
*A61B 6/00* (2006.01)
(Continued)

(52) U.S. Cl.
CPC ............. *A61B 19/5244* (2013.01); *A61B 19/56* (2013.01); *G06T 7/0075* (2013.01);
(Continued)

(58) Field of Classification Search
None
See application file for complete search history.

(56) References Cited

U.S. PATENT DOCUMENTS

| 4,219,842 A | 8/1980 | Miller |
| 4,603,231 A | 7/1986 | Reiffel et al. |

(Continued)

FOREIGN PATENT DOCUMENTS

| EP | 1168246 A2 | 1/2002 |
| JP | 2005118232 A | 5/2005 |

(Continued)

OTHER PUBLICATIONS

Anderson B.L., "Stereovision: Beyond Disparity Computation," Trends in Cognitive Sciences, 1998, vol. 2 (6), pp. 214-222.
(Continued)

*Primary Examiner* — Yingchung He

(57) ABSTRACT

An apparatus is configured to show telestration in 3-D to a surgeon in real time. A proctor is shown one side of a stereo image pair, such that the proctor can draw a telestration line on the one side with an input device. Points of interest are identified for matching to the other side of the stereo image pair. In response to the identified points of interest, regions and features are identified and used to match the points of interest to the other side. Regions can be used to match the points of interest. Features of the first image can be matched to the second image and used to match the points of interest to the second image, for example when the confidence scores for the regions are below a threshold value. Constraints can be used to evaluate the matched points of interest, for example by excluding bad points.

10 Claims, 17 Drawing Sheets

(51) Int. Cl.
  *A61B 19/00* (2006.01)
  *G06T 7/00* (2006.01)
  *G06T 11/00* (2006.01)
  *H04N 13/00* (2006.01)
  *H04N 13/02* (2006.01)
  *H04N 13/04* (2006.01)

(52) U.S. Cl.
  CPC ........ *G06T 11/00* (2013.01); *A61B 2019/5227* (2013.01); *A61B 2019/5231* (2013.01); *A61B 2019/5257* (2013.01); *A61B 2019/5265* (2013.01); *G06T 2207/10068* (2013.01); *G06T 2207/20096* (2013.01); *G06T 2207/20101* (2013.01); *G06T 2207/30004* (2013.01); *H04N 13/0003* (2013.01); *H04N 13/02* (2013.01); *H04N 13/04* (2013.01); *H04N 2013/0092* (2013.01)

(56) References Cited

U.S. PATENT DOCUMENTS

| | | | |
|---|---|---|---|
| 4,614,366 | A | 9/1986 | North et al. |
| 5,175,616 | A | 12/1992 | Milgram et al. |
| 5,217,003 | A | 6/1993 | Wilk |
| 5,428,192 | A | 6/1995 | Chen et al. |
| 5,432,528 | A | 7/1995 | Ritter |
| 5,457,754 | A | 10/1995 | Han et al. |
| 5,468,921 | A | 11/1995 | Blake et al. |
| 5,561,708 | A | 10/1996 | Remillard |
| 5,577,991 | A | 11/1996 | Akui et al. |
| 5,579,057 | A | 11/1996 | Banker et al. |
| 5,583,536 | A | 12/1996 | Cahill, III |
| 5,657,095 | A | 8/1997 | Yoshida et al. |
| 5,797,900 | A | 8/1998 | Madhani et al. |
| 5,808,665 | A | 9/1998 | Green |
| 5,836,869 | A | 11/1998 | Kudo et al. |
| 5,839,441 | A | 11/1998 | Steinberg |
| 5,855,583 | A | 1/1999 | Wang et al. |
| 5,950,629 | A | 9/1999 | Taylor et al. |
| 5,987,349 | A | 11/1999 | Schulz |
| 6,057,833 | A | 5/2000 | Heidmann et al. |
| 6,097,994 | A | 8/2000 | Navab et al. |
| 6,108,458 | A | 8/2000 | Hart |
| 6,122,541 | A | 9/2000 | Cosman et al. |
| 6,139,490 | A | 10/2000 | Breidenthal et al. |
| 6,159,016 | A | 12/2000 | Lubell et al. |
| 6,201,984 | B1 | 3/2001 | Funda et al. |
| 6,246,900 | B1 | 6/2001 | Cosman et al. |
| 6,424,885 | B1 | 7/2002 | Niemeyer et al. |
| 6,434,416 | B1 | 8/2002 | Mizoguchi et al. |
| 6,459,926 | B1 | 10/2002 | Nowlin et al. |
| 6,468,265 | B1 | 10/2002 | Evans et al. |
| 6,470,236 | B2 | 10/2002 | Ohtsuki |
| 6,484,049 | B1 | 11/2002 | Seeley et al. |
| 6,490,475 | B1 | 12/2002 | Seeley et al. |
| 6,493,608 | B1 | 12/2002 | Niemeyer |
| 6,522,906 | B1 | 2/2003 | Salisbury, Jr. et al. |
| 6,587,750 | B2 | 7/2003 | Gerbi et al. |
| 6,612,980 | B2 | 9/2003 | Chen et al. |
| 6,659,939 | B2 | 12/2003 | Moll et al. |
| 6,678,090 | B2 | 1/2004 | Spink |
| 6,714,839 | B2 | 3/2004 | Salisbury, Jr. et al. |
| 6,714,841 | B1 | 3/2004 | Wright et al. |
| 6,720,988 | B1 | 4/2004 | Gere et al. |
| 6,731,988 | B1 | 5/2004 | Green |
| 6,741,757 | B1 | 5/2004 | Torr et al. |
| 6,791,601 | B1 | 9/2004 | Chang et al. |
| 6,799,065 | B1 | 9/2004 | Niemeyer |
| 6,817,972 | B2 | 11/2004 | Snow |
| 6,837,883 | B2 | 1/2005 | Moll et al. |
| 6,839,456 | B2 | 1/2005 | Touzawa et al. |
| 6,856,324 | B2 | 2/2005 | Sauer et al. |
| 6,856,826 | B2 | 2/2005 | Seeley et al. |
| 6,856,827 | B2 | 2/2005 | Seeley et al. |
| 6,864,886 | B1 | 3/2005 | Cavallaro et al. |
| 6,866,671 | B2 | 3/2005 | Tierney et al. |
| 6,949,106 | B2 | 9/2005 | Brock et al. |
| 6,980,210 | B1 | 12/2005 | Weiglhofer et al. |
| 7,075,556 | B1 | 7/2006 | Meier et al. |
| 7,155,315 | B2 | 12/2006 | Niemeyer et al. |
| 7,194,118 | B1 | 3/2007 | Harris et al. |
| 7,277,120 | B2 | 10/2007 | Gere et al. |
| 7,689,014 | B2 | 3/2010 | Abovitz et al. |
| 7,907,166 | B2 | 3/2011 | Lamprecht et al. |
| 8,184,880 | B2 | 5/2012 | Zhao et al. |
| 8,218,727 | B2 | 7/2012 | Baumgart et al. |
| 8,423,182 | B2 | 4/2013 | Robinson et al. |
| 8,639,000 | B2 | 1/2014 | Zhao et al. |
| 8,830,224 | B2 | 9/2014 | Zhao et al. |
| 2002/0012460 | A1 | 1/2002 | Kochi et al. |
| 2002/0058929 | A1 | 5/2002 | Green |
| 2003/0151809 | A1 | 8/2003 | Takahashi et al. |
| 2003/0158463 | A1 | 8/2003 | Julian et al. |
| 2003/0210812 | A1 | 11/2003 | Khamene et al. |
| 2003/0216715 | A1 | 11/2003 | Moll et al. |
| 2004/0002642 | A1 | 1/2004 | Dekel et al. |
| 2004/0009459 | A1 | 1/2004 | Anderson et al. |
| 2004/0022418 | A1 | 2/2004 | Oota |
| 2004/0039485 | A1 | 2/2004 | Niemeyer et al. |
| 2004/0052333 | A1 | 3/2004 | Sayre et al. |
| 2004/0070615 | A1 | 4/2004 | Ewing et al. |
| 2004/0240725 | A1 | 12/2004 | Xu et al. |
| 2004/0263613 | A1 | 12/2004 | Morita |
| 2005/0054910 | A1 | 3/2005 | Tremblay et al. |
| 2005/0154288 | A1 | 7/2005 | Wang et al. |
| 2005/0179702 | A1 | 8/2005 | Tomlinson et al. |
| 2006/0013473 | A1 | 1/2006 | Woodfill et al. |
| 2006/0058919 | A1 | 3/2006 | Sommer |
| 2006/0087504 | A1 | 4/2006 | Meier et al. |
| 2006/0142657 | A1 | 6/2006 | Quaid et al. |
| 2006/0241414 | A1 | 10/2006 | Nowlin et al. |
| 2006/0258938 | A1 | 11/2006 | Hoffman et al. |
| 2007/0021738 | A1 | 1/2007 | Hasser et al. |
| 2007/0038080 | A1 | 2/2007 | Salisbury, Jr. et al. |
| 2007/0078334 | A1 | 4/2007 | Scully et al. |
| 2007/0138992 | A1 | 6/2007 | Prisco et al. |
| 2007/0147707 | A1 | 6/2007 | Coste-Maniere et al. |
| 2007/0161854 | A1 | 7/2007 | Alamaro et al. |
| 2007/0167702 | A1 | 7/2007 | Hasser et al. |
| 2007/0183041 | A1 | 8/2007 | McCloy et al. |
| 2007/0211927 | A1 | 9/2007 | Groszmann et al. |
| 2007/0265527 | A1 | 11/2007 | Wohlgemuth |
| 2008/0004603 | A1 | 1/2008 | Larkin et al. |
| 2008/0013809 | A1 | 1/2008 | Zhu et al. |
| 2008/0027356 | A1 | 1/2008 | Chen et al. |
| 2008/0033240 | A1 | 2/2008 | Hoffman et al. |
| 2008/0046122 | A1 | 2/2008 | Manzo et al. |
| 2008/0065109 | A1 | 3/2008 | Larkin |
| 2008/0125794 | A1 | 5/2008 | Brock et al. |
| 2008/0177284 | A1 | 7/2008 | Lee et al. |
| 2008/0285724 | A1 | 11/2008 | Dehler |
| 2009/0015004 | A1 | 1/2009 | Long |
| 2009/0036902 | A1 | 2/2009 | DiMaio et al. |
| 2009/0046146 | A1 | 2/2009 | Hoyt |
| 2009/0069821 | A1 | 3/2009 | Farritor et al. |
| 2009/0088634 | A1 | 4/2009 | Zhao et al. |
| 2009/0088773 | A1 | 4/2009 | Zhao et al. |
| 2009/0088897 | A1 | 4/2009 | Zhao et al. |
| 2009/0171332 | A1 | 7/2009 | Bonneau |
| 2009/0171371 | A1 | 7/2009 | Nixon et al. |
| 2009/0192523 | A1 | 7/2009 | Larkin et al. |
| 2009/0192524 | A1 | 7/2009 | Itkowitz et al. |
| 2009/0248036 | A1 | 10/2009 | Hoffman et al. |
| 2009/0248041 | A1 | 10/2009 | Williams et al. |
| 2009/0268010 | A1 | 10/2009 | Zhao et al. |
| 2009/0268011 | A1 | 10/2009 | Scott et al. |
| 2009/0268012 | A1 | 10/2009 | Scott et al. |
| 2009/0268015 | A1 | 10/2009 | Scott et al. |
| 2009/0270678 | A1 | 10/2009 | Scott et al. |
| 2009/0326553 | A1 | 12/2009 | Mustufa et al. |
| 2010/0149183 | A1 | 6/2010 | Loewke et al. |
| 2010/0168562 | A1 | 7/2010 | Zhao et al. |
| 2010/0168763 | A1 | 7/2010 | Zhao et al. |

(56) References Cited

U.S. PATENT DOCUMENTS

| | | | |
|---|---|---|---|
| 2010/0169815 | A1 | 7/2010 | Zhao et al. |
| 2010/0204713 | A1 | 8/2010 | Ruiz Morales |
| 2010/0228249 | A1 | 9/2010 | Mohr et al. |
| 2010/0245541 | A1 | 9/2010 | Zhao et al. |
| 2010/0317965 | A1 | 12/2010 | Itkowitz et al. |
| 2010/0318099 | A1 | 12/2010 | Itkowitz et al. |
| 2010/0331855 | A1 | 12/2010 | Zhao et al. |
| 2011/0050852 | A1 | 3/2011 | Lamprecht et al. |

FOREIGN PATENT DOCUMENTS

| | | | |
|---|---|---|---|
| JP | 2008245838 | A | 10/2008 |
| WO | WO-0129681 | A1 | 4/2001 |
| WO | WO-0229723 | A1 | 4/2002 |
| WO | WO-03045222 | A2 | 6/2003 |
| WO | WO-2004029786 | A1 | 4/2004 |
| WO | WO-2005037093 | A1 | 4/2005 |
| WO | WO-2005102202 | A1 | 11/2005 |
| WO | WO-2005119505 | A2 | 12/2005 |
| WO | WO-2006124388 | A1 | 11/2006 |
| WO | WO-2006131373 | A2 | 12/2006 |
| WO | WO-2007120351 | A2 | 10/2007 |
| WO | WO-2008079546 | A2 | 7/2008 |
| WO | WO-2009025783 | A1 | 2/2009 |
| WO | WO-2009045827 | A2 | 4/2009 |
| WO | WO-2009085616 | A1 | 7/2009 |

OTHER PUBLICATIONS

Ayala, Hugo M, et al., "Wear of Oil Containment Elastomer in Abrasive Slurries," 1998, pp. 9-21, vol. 220—Issue. 1, Elsevier Science.
Barron, J.L. et al., "Performance of optical flow techniques," Intl. J. of Computer Vision, 1994, pp. 43-77, vol. 12—Issue. 1.
Benson, K. Blair, "Television Engineering Handbook," 1986, pp. 14.68-14.72, McGraw-Hill.
Boeckeler Instruments, Inc., "Pointmaker PVI-44 Compact Video Marker Manual," Section One, 2006, pp. 3-32.
Boeckeler Instruments, Inc., "Pointmaker PVI-X90 Presentation System," specification sheet, www.pointmaker.com, © 1994-2004, 2 pages.
Brown, Myron M. et al., "Advances in Computational Stereo," IEEE Transactions on Pattern Analysis and Machine Intelligence (PAMI), 2003, pp. 993-1008, vol. 25 Issue, IEEE.
Carter, William, "The advantage of single lens stereopsis," Stereoscopic Displays and Applications III, 1992, pp. 204-210, vol. 1669, SPIE.
Co-pending U.S. Appl. No. 61/203,975, filed Dec. 31, 2008.
Co-pending U.S. Appl. No. 61/204,082, filed Dec. 31, 2008.
Fischler, Martin A. and Robert C. Bolles, "Random sample consensus: a paradigm for model fitting with applications to image analysis and automated cartography," Communications of the ACM, vol. 24, No. 6, Jun. 1981, pp. 381-395.
FR0611491 Preliminary Search Report, mailed Mar. 26, 2010, 6 pages.
Guthart, Gary S. et al., "The IntuitiveT telesurgery system: overview and application," Proceedings of the 2000 IEEE International Conference on Robotics & Automation, 2000, pp. 618-621, vol. 1, IEEE.
Hart, Douglas P., "Second-Order Correlation," YAYOI Symposium on Particle Imaging Velocimetry (VSJ-SPIE98 Post-Conference Symposium), 1998, 14 pages.
Hart, Douglas P., "High speed PIV analysis using compressed image correlation," Journal of Fluids Engineering, 1998, pp. 463-470, vol. 120.
Hart, Douglas P., "Sparse array image correlation," 8th International Symposium on Applications of Laser Techniques to Fluid Mechanics, 1996, pp. 53-74, vol. 1 (Session 1).
Hart, Douglas P., "PIV Error Correction," 9th International Symposium on Applications of Laser Techniques to Fluid Mechanics, Jul. 13-16, 1998, Lisbon, Portugal, in Laser Techniques Applied to Fluid Mechanics: Selected Papers from the 9th International Symposium, 1998, pp. 19-36.

Hart, Douglas P., "PIV error correction," Experiments in Fluids, 2000, pp. 13-22, vol. 29—Issue 1, Springer-Verlag.
Hart, Douglas P., "Successive Approximation PIV Analysis to Achieve High Accuracy," Resolution, and Speed, The 13th U.S. National Congress of Applied Mechanics, 1998, 1 page.
Hart, Douglas P., "Super-Resolution PIV Processing by Recursive Correlation," Journal of Visualization,The Visualization Society of Japan, 2000, pp. 187-194, vol. 10.
Hidrovo, Carlos H. et al., "2-D thickness and Temperature Mapping of Fluids by Means of Two Dye Laser Induced Fluorescence Ratiometric Scheme," Proceedings of the 3rd Pacific Symposium on Flow Visualization and Image Processing, 2001, 30 pages.
Hidrovo, Carlos H. et al., "2-D thickness and Temperature Mapping of Fluids by Means of Two-Dye Laser Induced Fluorescence Ratiometric Scheme,"Journal of Flow Visualization and Image Processing, 2002, pp. 171-191, vol. 9.
Hidrovo, Carlos H. et al., "Emission Reabsorption Laser Induced Fluorescence for Film Thickness Measurement," Measurement Science and Technology, 2001, pp. 467-477, vol. 12—Issue 4, Institute of Physics Publishing.
Horn, Berthold K.P. et al., "Determining Optical Flow, Artificial Intelligence," 1981, pp. 185-203, vol. 17.
Huang, Hayden et al., "Quantified flow Characteristics in a Model Cardiac Assist Device," Measurement and Instrumentation Forum, ASME Fluids Engineering Division Summer Meeting, Jun. 22-26, 1997, 6 pages.
Jojic, Nebojsa et al., "Tracking Self-Occluding Articulated Objects in Dense Disparity Maps," IEEE International Conference on Computer Vision, Corfu, 1999, pp. 123-130, vol. 1, IEEE.
Kavoussi, Louis R. et al., "Telerobotic Assisted Laparoscopic Surgery: Initial Laboratory and Clinical Experience," Urology, Jul. 1994, pp. 15-19, vol. 44—Issue 1.
Keith, Jack, Ideo Demystified, A Handbook for the Engineer, 1993, pp. 338-356, HighText Publications, Inc., Solana Beach, CA, USA, ISBN: 1-878707-09-4.
Keramas, James G., "Robot Technology Fundamentals," 1999, pp. 193-219.
Kim, Miriam et al., "Computer Assisted 3D Measurements for Micro-Surgery," Proceedings of the Human Factors and Ergonomics Society 41st Annual Meeting, 1997, pp. 787-791, Human Factors and Ergonomics Society.
Kim, Yoon Sang, "Surgical Telementoring Initiation of a Regional Telemedicine Network: Projection of Surgical Expertise in the WWAMI Region," 3rd 2008 International Conference on Convergence and Hybrid Information Technology (ICCIT 08), Nov. 11-13, 2008, Busan, Korea, vol. 1, pp. 974-979, IEEE.
Kosaka, Akio et al., "Augmented Reality System for Surgical Navigation Using Robust Target Vision," IEEE Conference on Computer Vision and Pattern Recognition, 2000, vol. 2, pp. 187-194.
Lammerding, J. et al., "Monocular 3-D Magnetic Bead Microrheometry," 11th International Symposium on Application of Laser Techniques to Fluid Mechanics, 2002, 4 pages.
Lee, Benjamin R. et al., "A novel method of surgical instruction: international telementoring," World Journal of Urology, 1998, pp. 367-370, vol. 16—Issue 6, Springer Berlin / Heidelberg.
Lee C.H., et al., "Purification and Characterization of a Polysome-associated Endoribonuclease that Degrades c-myc mRNA in Vitro," The Journal of Biological Chemistry, 1998, vol. 273 (39), pp. 25261-25271.
Lin, Cheng-Hsien et al., "Ultrasound motion estimation using a hierarchical feature weighting algorithm," Computerized Medical Imaging and Graphics, 2007, vol. 31, pp. 178-190, Elsevier.
Link, Richard E. et al., "Telesurgery: Remote Monitoring and Assistance During Laparoscopy," Urol Clin North Am, 2001, pp. 177-188, vol. 28—Issue 1, Sanders.
Lowe, David G., "Distinctive Image Features from Scale-Invariant Keypoints," International Journal of Computer Vision, vol. 60, No. 2, Nov. 2004, pp. 91-110.
Micali, S. et al., "Feasibility of telementoring between Baltimore (USA) and Rome (Italy): the first five cases," J Endourol, 2000, pp. 493-496, vol. 14—Issue 6.

(56) References Cited

OTHER PUBLICATIONS

Moore, R.G. et al., "Telementoring of laparoscopic procedures: Initial clinical experience," Surgical Endoscopy, 1996, pp. 107-110, vol. 10—Issue 2, Springer-Verlag.

Office Action mailed Dec. 12, 2013 for Japanese Application 2012516111 filed Jun. 3, 2010.

Office Action mailed Dec. 20, 2013 for Chinese Application 201080027164.3 filed Jun. 3, 2010.

Official Action mailed Aug. 8, 2012 for JP Application No. 2006335952 filed Dec. 13, 2006.

PCT/US06/62381 International Search Report, mailed Jan. 2, 2008, 1 page.

PCT/US06/62381 Written Opinion of the International Search Authority, mailed Jan. 2, 2008, 6 pages.

PCT/US09/68427 International Search Report and Written Opinion of the International Searching Authority, mailed Nov. 23, 2010, 20 pages.

PCT/US09/68427 Partial International Search Report, mailed Jun. 18, 2010, 6 pages.

PCT/US10/35402 International Search Report and Written Opinion of the International Searching Authority, mailed Aug. 2, 2010, 16 pages.

PCT/US10/37293 International Search Report and Written Opinion of the International Searching Authority, mailed Nov. 29, 2010, 19 pages.

Rafiq A., et al., "Digital Video Capture and Synchronous Consultation in Open Surgery," Annals of Surgery, 2004, vol. 239 (4), pp. 567-573.

Rafiq, Azhar et al., "SOCRATES: Telementoring for Telerobotics", and Todd Drasin et al., "Using Telerobots as Assistant Surgeons," Chapters 11 and 26: Primer of Robotic & Telerobotic Surgery, Garth H. Ballentyne et al., 2004, Ilppincott Williams & Wilkins, pp. 78-85 and 188-195.

Rohaly, Janos et al., "High Resolution Ultrafast 3D Imaging," Proceedings of Photonics West 2000: Three Dimensional Image Capture and Application III, 2000, pp. 2-10, vol. 3958, SPIE.

Rohaly, Janos et al., "Monocular 3-D Active Micro-PTV," 4th International Symposium on Particle Image Velocimetry, 2001, pp. 1-4, paper No. 1147.

Rohaly, Janos et al., "Reverse Hierarchical PIV Processing," 4th International Symposium on Particle Image Velocimetry, 2001, 16 pages, paper No. 1009.

Saga, Sato et al., "A Method for Modeling Freehand Curves—the Fuzzy Spline Interpolation," Systems and Computers in Japan, Sep. 26, 1995, vol. 26, Issue 10, pp. 77-87, Scripta Technica, Inc.

Scharstein D., et al., A Taxonomy and Evaluation of Dense Two-Frame Stereo Correspondence Algorithm, Proceedings of the IEEE Workshop on Stereo and Multi-Baseline Vision, 2001, 10 pages.

Schulam Peter G. et al., "Telesurgical mentoring: Initial clinical Experience," Surgical Endoscopy, 1997, pp. 1001-1005, vol. 11, Springer-Verlag.

See, William A. et al., "Predictors of laparoscopic complications after formal training in laparoscopic surgery," Journal of the American Medical Association, 1993, pp. 2689-2692, vol. 270—Issue 22.

Stefano L.D., et al., "A Fast Area-Based Stereo Matching Algorithm," Image and Vision Computing, 2004, vol. 22, pp. 983-1005.

Stoianovici, Dan, "Robotic tools for minimally invasive urologic surgery," Chapter in Complications of Urologic Laparoscopic Surgery: Recognition, Management and Prevention, published 2005 by Taylor Francis, paper dated Dec. 2002, 17 pages.

Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.

Taylor, Russell H., et al., "An overview of computer-integrated surgery at the IBM Thomas J. Watson Research Center," IBM J Research and Development, 1996, pp. 163-183, vol. 40, Issue 2, IBM Corp.

Thirouard, Benoist et al., "Investigation of Oil Transport Mechanisms in the Piston Ring Pack of a Single Cylinder Diesel Engine," Using Two-Dimensional Laser-Induced Fluorescence, SAE Transactions: Journal of Fuels and Lubricants, 1998, pp. 2007-2015, vol. 107—Issue 4.

Trucco, E. et al., "Real-Time Disparity Maps for Immersive 3-D Teleconferencing by Hybrid Recursive Matching and Census Transform," Dept. of Computing and Electrical Engineering, 2001, 9 pages.

Tzovaras, Dimitrios et al., "Disparity field and depth map coding for multiview 3D image generation," Signal Processing: Image Communication, 1998, pp. 205-230, vol. 11, Elsevier.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wu, Chun-Hong et al., "Depth Mapping of Integral Images through Viewpoint Image Extraction with a Hybrid Disparity Analysis Algorithm," Journal of Display Technology, Mar. 2008, vol. 4, Issue No. 1, pp. 101-108, IEEE.

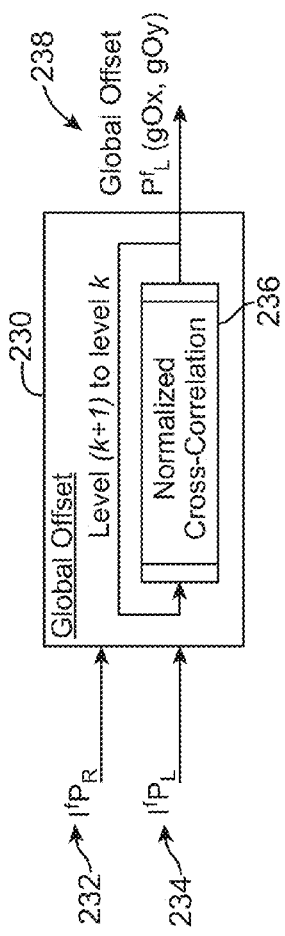
FIG. 2C
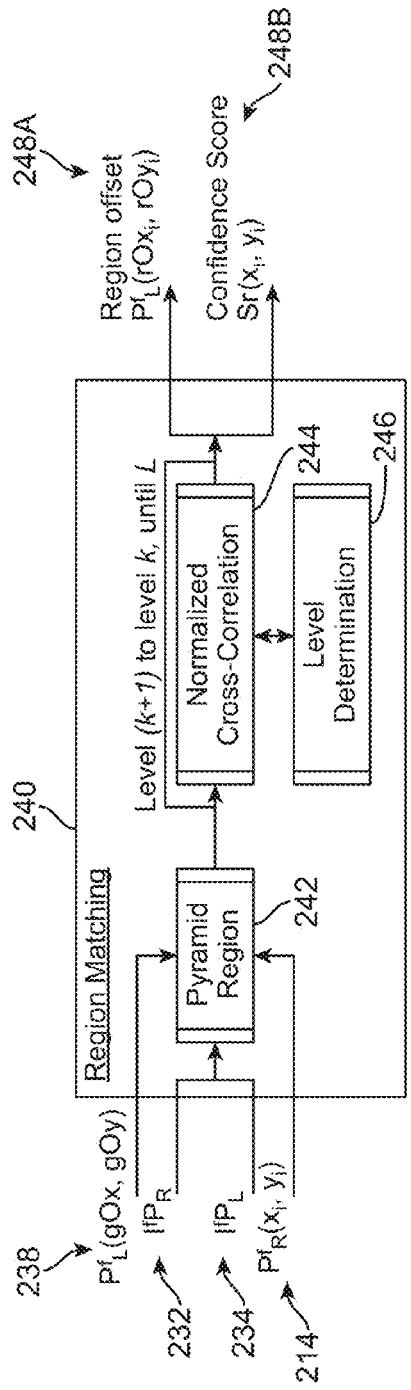
FIG. 2D1

FIG. 2D2

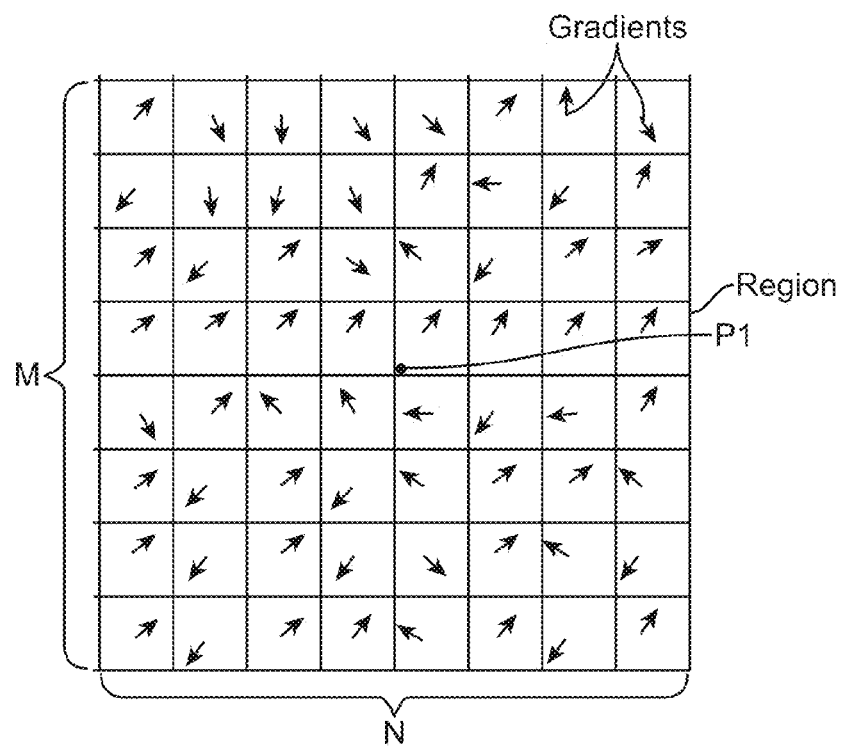
FIG. 2E1
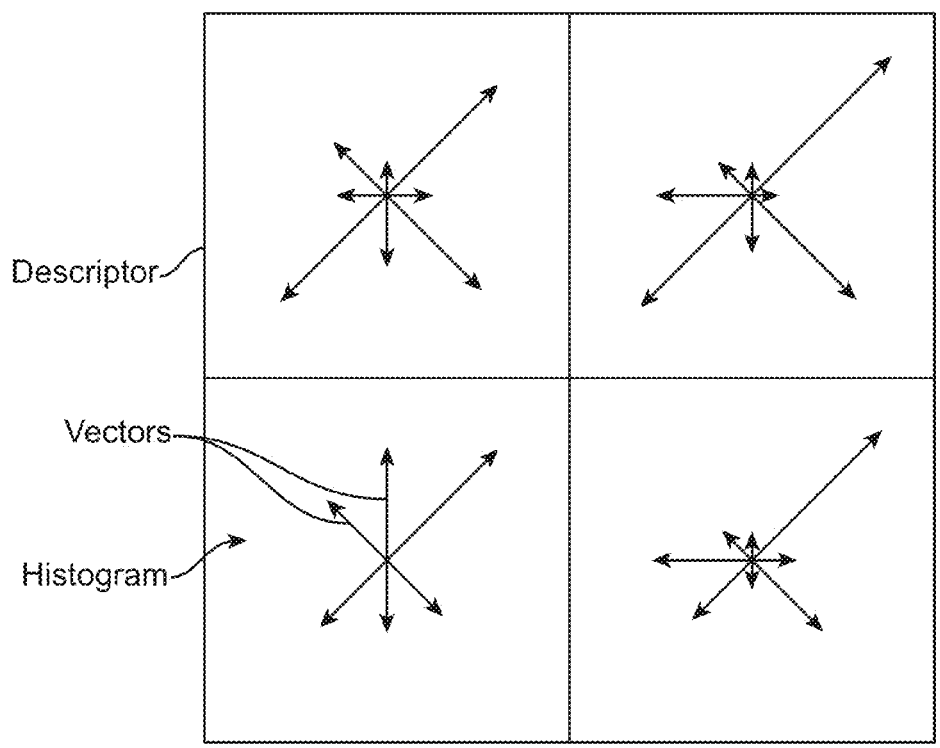
FIG. 2E2

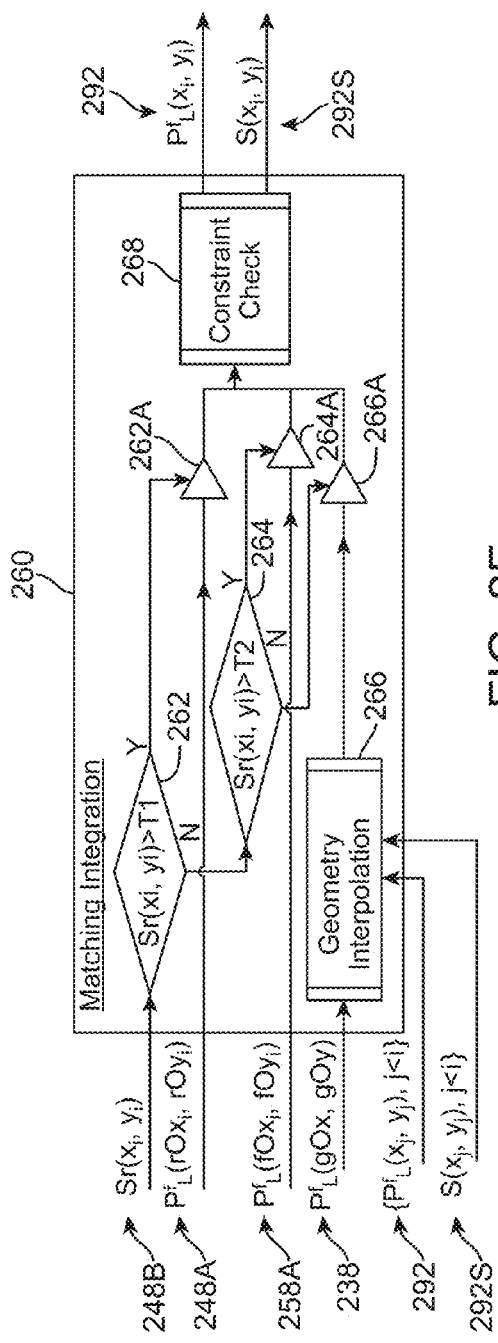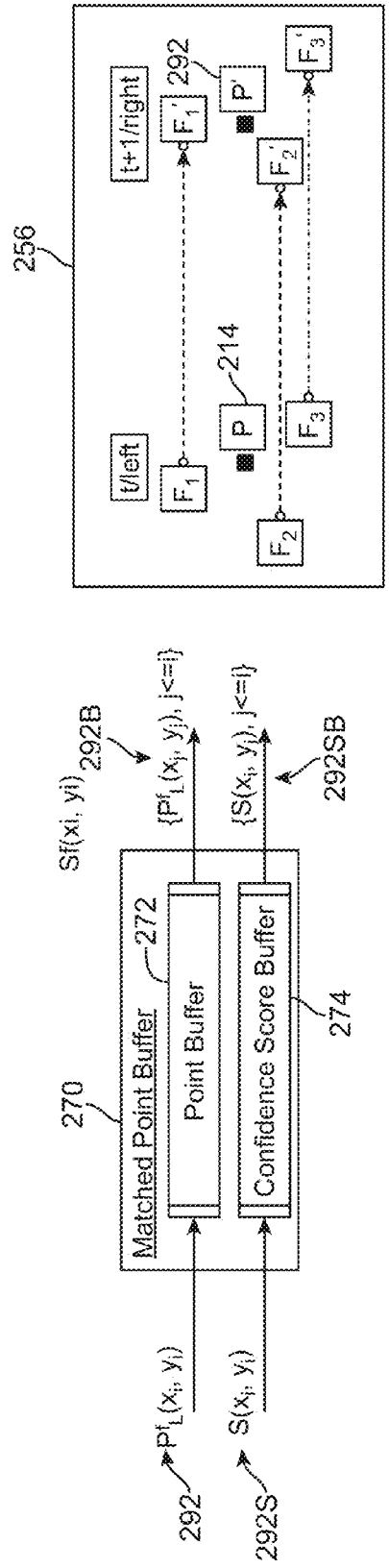

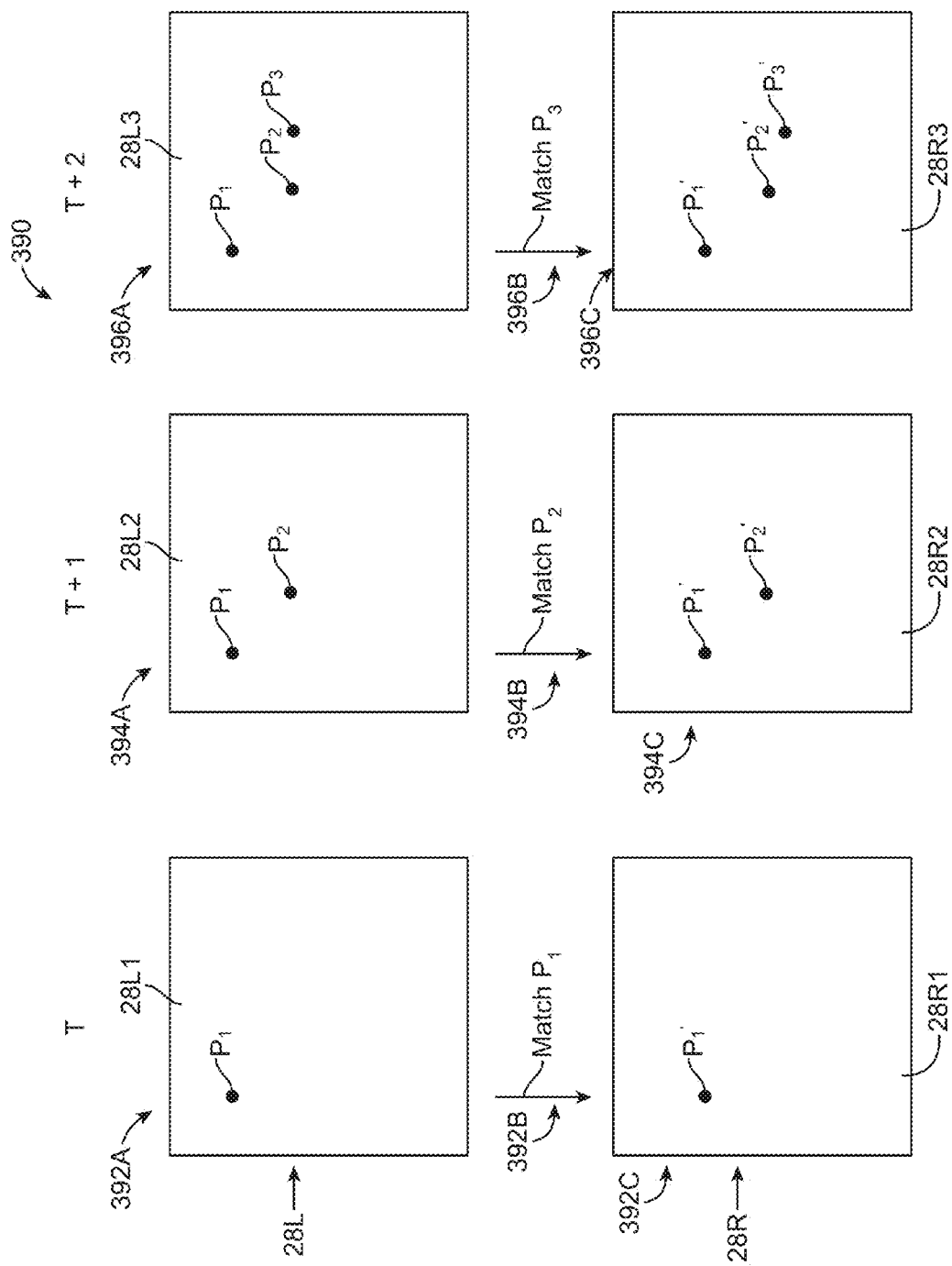

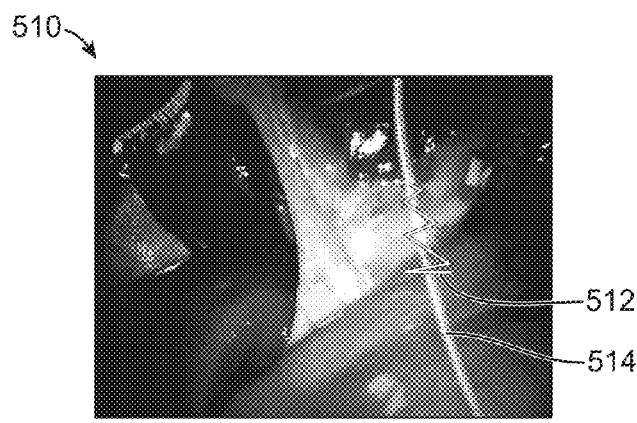
Left Image w. Surgeon's Drawing
FIG. 5A
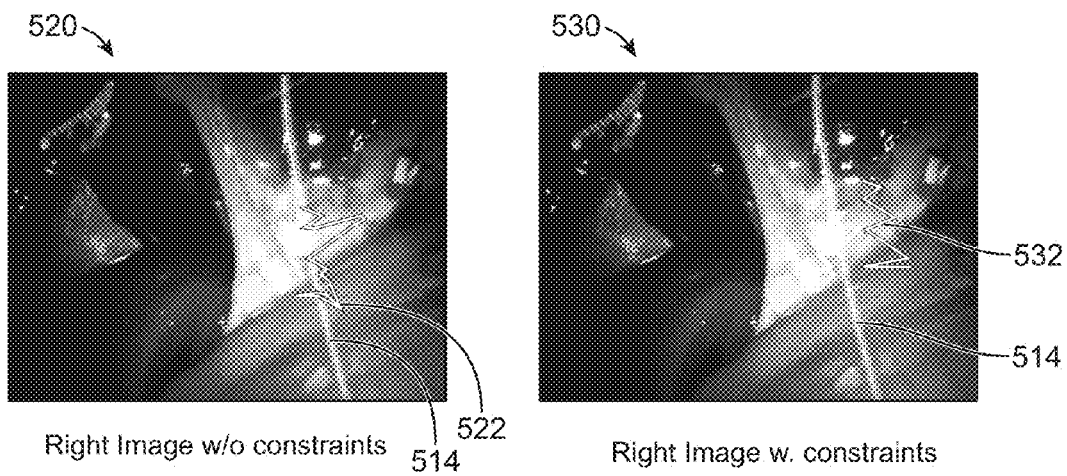
Right Image w/o constraints
FIG. 5B
Right Image w. constraints
FIG. 5C

EFFICIENT 3-D TELESTRATION FOR LOCAL AND REMOTE ROBOTIC PROCTORING

CROSS REFERENCE TO RELATED APPLICATIONS

This application is a continuation of U.S. application Ser. No. 12/465,020 (filed May 13, 2009), now U.S. Pat. No. 8,830,224, which claims the benefit under 35 U.S.C. §119(e) of provisional U.S. App. No. 61/204,046 (filed Dec. 31, 2008), each of which is incorporated herein by reference.

The subject matter of the present application is related to U.S. application Ser. No. 12/465,029 (filed May 13, 2009), now U.S. Pat. No. 8,184,880, and to U.S. App. No. 61/204,082 (filed Dec. 31, 2008), each of which is incorporated herein by reference.

BACKGROUND

The present invention relates to systems, methods, and devices for imaging and image processing. Although specific reference is made to telestration and tissue tracking with a three-dimensional (3-D) display, embodiments of the present application may be useful in many fields that match images, for example image guided surgery.

The basic goal of image guided surgery (IGS) is to enhance a surgeon's experience and surgical results by providing real time information derived from single or multiple imaging modalities. With IGS, the surgeon uses indirect visualization of tissue to operate. The indirect visualization of tissue can come from many image sources, and IGS can utilize images from sources such as endoscopic, fiber optic, x-ray, computerized tomography (CT), magnetic resonance imaging (MRI), and ultrasound. IGS can be used for surgery, training, and simulation. Two particular benefits of IGS can be improved visualization for easier on-line diagnostics and improved localization for reliable and precise surgery. Many forms of guided surgery can present stereo images of the tissue to the surgeon such that the surgeon can visualize the tissue in 3-D. At least some of the known IGS methods can benefit from the matching of images, and at least some of the known methods for matching images can provide less than ideal results in at least some instances, for example when images have few matching features and at least some of the features are not reliable.

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A known form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch or less) incisions to provide entry ports for laparoscopic instruments.

Laparoscopic surgical instruments generally include a laparoscope or an endoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, image capture lenses, and needle holders, for example.

To perform surgical procedures, the surgeon passes these working tools or instruments through cannula sleeves to an internal surgical site and manipulates them from outside the abdomen. The surgeon views the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a control console. While viewing a 3-D image of the surgical site on a suitable viewer or display, the surgeon performs the surgical procedures on the patient by manipulating master input or control devices of the control console. Each of the master input devices controls the motion of a servomechanically operated surgical instrument. During the surgical procedure, the telesurgical system can provide mechanical actuation and control of a variety of surgical instruments or tools having end effectors that perform various functions for the surgeon, e.g., holding or driving a needle, grasping a blood vessel, dissecting tissue, or the like, in response to manipulation of the master input devices.

In many instances, it can be helpful if the surgeon is able to communicate and even receive instruction from another surgeon. Three-dimensional stereo telestration has been proposed to facilitate surgeon communication and teaching. Work in relation to embodiments of the present invention suggests that known methods and apparatuses for telestration during surgery may be less than ideal. At least some of the known telestration methods rely on image processing for telestration, and in at least some instances the surgical images can present significant challenges due to the complexity of a surgical field. The surgical field can produce sparse images in which at least a portion of the images is sparse in texture, features, or contrast, such that matching of the images can be difficult. For example, a surgical field may contain tissues that are smooth and may have specular reflections, and there may be instruments shining and at different depths. In addition, blood and other medical liquids make image matching a challenging task. In at least some instances the images may comprise few features, and at least some of these features may be unreliable for matching, so that reliable matching of the images can be difficult. Further, tissue can move and surgery occurs in real time such that it would be helpful to provide telestration in real time, and some of the known image matching methods may have at least some delay when images are processed. At least some of the known image matching methods may attempt to match all of the pixels in an entire image, which can result in delay in at least some instances. For example, at least some known image matching methods may generate a disparity map of an entire image, which can be computationally expensive and make real time 3-D telestration difficult in at least some instances. Consequently, at least some of the known methods of telestration may provide less than ideal results.

Accordingly, improved methods and systems providing improved image matching and telestration would be desirable, particularly those which work well in complex surgical fields.

SUMMARY

Embodiments and aspects of the present invention provide improved 3-D telestration that can reliably and efficiently show telestration in 3-D to a user, for example a surgeon, in real time with surgical images that may include sparse and unreliable image markers and textures, even when a second user, for example a proctor, draws a telestration line in poorly defined regions of an image. The proctor can be shown one side (i.e., right or left) of a stereo pair of images. The proctor can draw a telestration mark, for example a telestration line, on the one side with an input device, such that points of interest of the first image are input with the input device. The points of interest from the first image are selectively identified for matching to the second image of the stereo pair. This selective identification of the points of interest from the first image can significantly reduce the number of points matched and can provide 3-D telestration in real time, for example without determining a disparity map. The points of interest can be selectively identified for matching in many ways, for example by selecting raw data points or by fitting raw input data points to a curve, such as a spline.

The selectively identified points of interested can be matched to the second image with selective matching. The selective matching can match the selectively identified points with matching that is appropriate to the local characteristics of the image. The selective matching may include at least one of region matching, feature matching, feature interpolation, or interpolation of previously matched points. For example, regions can be identified in response to the selected points of interest and used to match the selectively identified points of interest. Region matching scores can be determined when the regions are matched, and for regions that are not sufficiently matched, the features of the insufficiently matched regions can be determined and matched to the second image, such that these features are used to match the points of interest to the second image. This use of feature matching in response to insufficient region matching provides more complex matching, when appropriate, so as to optimize robustness and speed. For example, with sparse surgical images at least some of the points of a sparse image can be unreliable, and the use of feature matching in response to region matching can improve reliability of the matched points of interest. Constraints, for example soft epi-polar constraints and focus constraints can be used to evaluate the matched points of interest, for example by excluding bad points. The constraints can be very helpful when the surgical field includes interfering objects at different depths from the tissue, for example out of focus sutures that can interfere with the image matching for telestration. The constraints may also be used to improve searching for matched regions or features to determine the matched points of interest, for example by constraining dimensions of the search based on the constraint. Interpolation may also be used, for example when confidence scores for feature matching are below a threshold value or bad points are excluded by the constraints.

In a first aspect, embodiments of the present invention provide a method of 3-D telestration for a user. Selected points of interest of a first image are identified. The first image is displayed on a user display with a first telestration mark at the selected points of interest. The selected points of interest are selectively matched to a second image to determine matched points of interest in response to the identification of the selected points of interest. The second image is displayed on the user display with a second telestration mark at the matched points of interest such that the first telestration mark and the second telestration mark appear as a single 3-D telestration mark to the user.

In many embodiments, the selected points of interest of the first image are matched to the second image without a disparity map, so that no matching of the first image to the second image occurs throughout most of the first image and most of the second image.

In many embodiments, the points of interest of the first image are input with an input device to draw the first telestration mark and wherein the selected points of interest are identified from the points of interest.

The points of interest selected for image matching can be identified in many ways. The selected points of interest can be identified by at least one of selecting raw data points, fitting raw data points to a curve, or interpolating raw data points. For example, raw data points can be identified, such that the identified raw data points of the first image are selected for matching to the second image. Identifying the points of interest may comprise fitting the raw data points to a curve, for example a spline, such that the curve comprises the selected points of interest. Identifying the points of interest may comprises interpolating the raw data points to determine an interpolated data point of the first image, such that the interpolated data point of the first image is matched to the second image.

The selected points of interest can be selectively matched to the second image in many ways. The selective matching of the selected points of interest may include at least one of selectively matching regions, selectively matching features, selectively interpolating features, or selectively interpolating previously matched points of interest. For example, the selective matching may comprise selectively matching the regions, in which the regions are identified from the first image in response to the selected points of interest, and corresponding matched regions of the second image determined from the regions. The regions can be matched to the corresponding matched regions to determine the locations of the matched points of interest. Each of the regions from the first image may comprise a portion of the first image so as to include at least one of the selected points of interest within the region, and each of the corresponding matched regions may comprises a portion of the second image so as to include at least one of the matched points of interest within the corresponding matched region of the second image. Region match confidence scores can be determined for each of the regions matched to the second image.

In many embodiments, features are selectively matched for each of the regions having a low confidence score. Selectively matching the features may comprise identifying the features in response to the selected points of interest, and the features can be matched to the second image to determine the matched points of interest. Each of the features can be identified with a descriptor comprising at least one vector having a location, an orientation, and a magnitude, wherein the at least one vector is determined in response to a gradient of intensities of pixels of the first image. Feature match confidence scores can be determined for each of the features matched to the second image.

In many embodiments, successfully matched features are interpolated to determine the matched points of interest for features having low feature match confidence scores. The previously matched points of interest can be interpolated to determine the matched points of interest for each point of interest having a low feature match confidence score, for example when the successfully matched features are insufficient for interpolation.

In many embodiments, the first image and the second image comprise a pair of real time stereoscopic images from a robotic surgery system, and the pair of stereoscopic images are shown in three dimensions to the user. The first image comprises a first series of real time digital images, and the second image comprises a second series of real time digital images, such that the identified points of interest correspond to identified points of the first series of real time digital images and the matched points of interest correspond to matched points of the second series of real time digital images.

In another aspect, embodiments of the present invention provide a 3-D telestration display method. A pair of stereoscopic images is captured, in which the pair comprises a first image and a second image. A telestration input is received for the first image. Selected first points of interest of the first image are identified from the telestration input. The selected first points of interest in the first image are matched to corresponding second points of interest in the second image, and output to a stereoscopic display. The stereoscopic display comprises the first image with a first telestration mark associated with the first selected points of interest. The stereoscopic display also comprises the second image with a second telestration mark associated with the second points of interest. The first image and the second images appear as a single 3-D image in the display, and the first and second telestration marks appear as a single 3-D telestration mark in the display.

In another aspect, embodiments of the present invention provide an apparatus to show 3-D telestration a user. The apparatus comprises a source of images comprising a first image and a second image, for example a pair of stereoscopic images. A first user display comprises a first display and a second display to present the first image and the second image to the user in a 3-D image. A second user display is configured to show at least one of the first image or the second image to a second user. A second user input device is configured to receive input from the second user to draw a telestration mark on the first image shown on the second user display. A processor system comprising a tangible medium is configured to receive the input from the second user input device, identify selected points of interest of the first image in response to the input, and selectively match the selected points of interest to the second image to determine matched points of interest. The processor system is configured to display a second telestration mark at the matched points of interest such that the first telestration mark and the second telestration mark appear as a single 3-D telestration mark to the user.

BRIEF DESCRIPTION OF THE DRAWINGS

FIG. 2C shows a global offset as in FIG. 2A;

FIG. 2D1 shows region matching as in FIG. 2A;

FIG. 2D2 shows level determination as in FIG. 2A and FIG. 2D1;

FIG. 2E1 shows an identified point of interest as in FIG. 1F for region and feature matching as in FIGS. 2D1, 2D2, and 2E;

FIG. 2E2 shows a feature comprising a key point descriptor for the region as in FIG. 2E1;

FIG. 2F shows matching integration as in FIG. 2A;

FIG. 2G shows a matched point buffer for matched points of interest as in FIG. 2A and FIG. 2F;

FIG. 2H shows interpolation of features as in FIG. 2A and FIG. 2E;

FIG. 3C shows matching of points from a first series of images to a second series of images;

FIG. 5A shows a left image with the proctor surgeon's drawing showing points of interest, in accordance with embodiments;

FIG. 5B shows a right image with matched points of interest from FIG. 5A in which the points of interest are matched without constraints; and FIG. 5C shows a right image with matched points of interest from FIG. 5A in which the points of interest are matched with soft epi-polar and focus constraints, in accordance with embodiments.

DETAILED DESCRIPTION

Figure 1A:
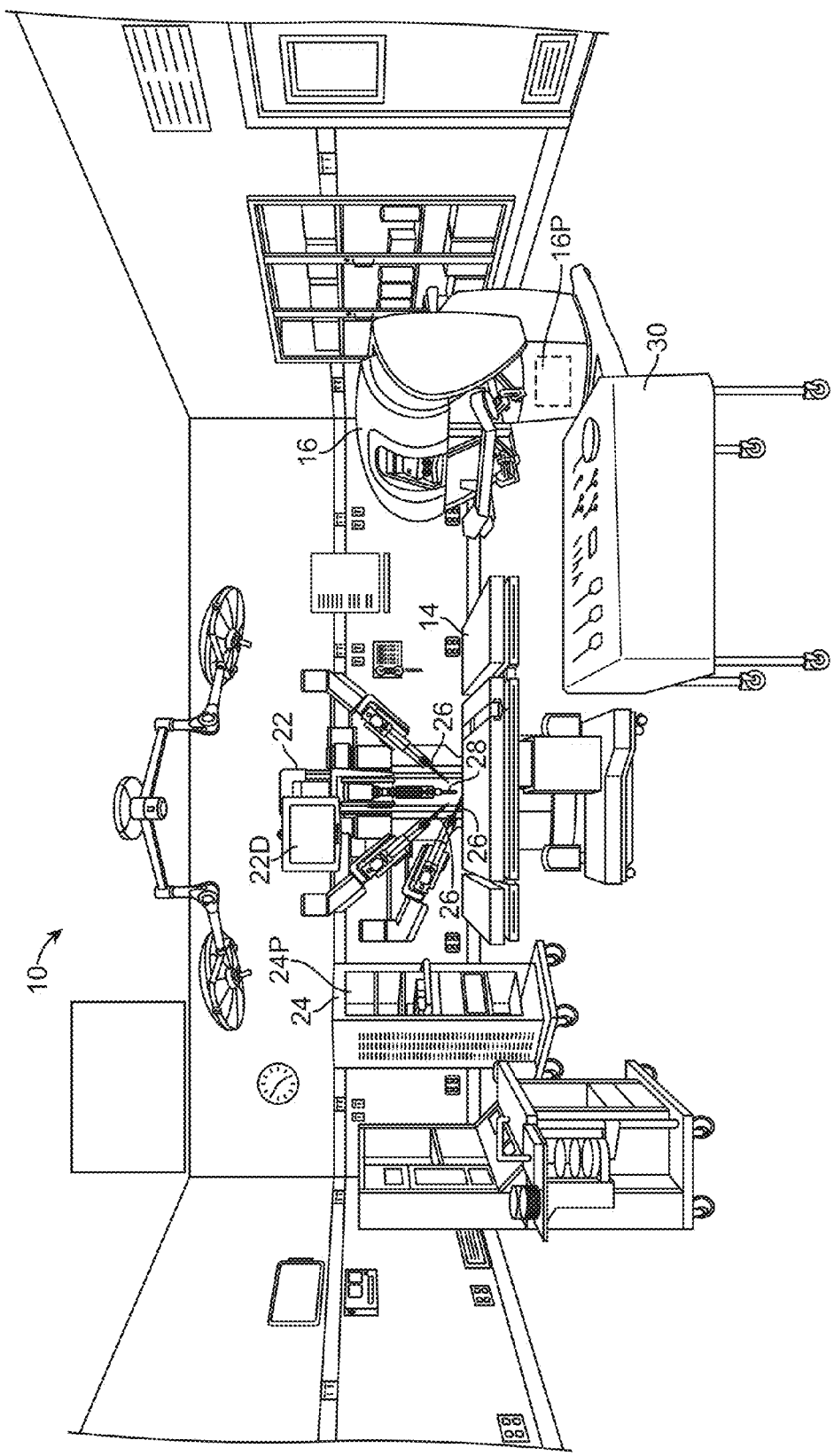
FIGS. 1A and 1B are perspective and plan views, respectively, of a minimally invasive robotic surgery system being used to perform a surgery, in accordance with embodiments.

In accordance with embodiments, improved methods, systems, and devices are provided for improved image matching. Such methods, systems, and devices can be particularly advantageous when employed during minimally invasive robotic surgery, for example when used for telestration and tissue tracking functions with minimally invasive robotic surgery.

Selective image matching as described herein can provide robust image matching so as to enable many forms of image guided surgery without significant added operational inconvenience and/or added equipment. For example, the selective and robust matching of images as described herein can be advantageous for many aspects of vision-related applications such as robotic surgery. The image matching described herein can reliably and accurately match sparse images from the surgical field in which at least a portion of the images is sparse in texture, features or contrast. Embodiments of the present invention allow points to be flexibly selected, for example, by surgeons, based on clinical importance, or by equal sampling rather than based on image matching reliability. For example, a proctor surgeon can draw a telestration mark on a first image shown on a display to select points of interest, and the points of interest can be identified and matched to a second image, even when the identified points of interest correspond to sparse regions of the first image with little contrast.

With many of the telestration embodiments described herein, there are two principle individuals, in which a first user is shown telestration marks made by a second user. The second user may be referred to a telestrator who generates telestration marks visible to the first user. The first user may be a student and the second user a may be an instructor who teaches the first user with the telestration marks. In many embodiments, the first user is the operator surgeon who is operating the robot to perform the surgery, and the second user is the proctor surgeon who is using the telestration input device so as to instruct the first user. Although specific reference is made to a proctor surgeon and an operator surgeon, embodiments of the present invention will find use in many applications where a first person communicates to a second with telestration. The first user can input points of interest that can be selectively identified for matching.

Once points of interest have been selected from the first image, points of interest are identified for matching to a second image in response to the selected points of interest. The identified points of interest are selectively matched to the second image, such that only a portion of the first image and the second images are processed. The identified points of interest can be determined in many ways, for example by at least one of selecting from among raw points of interest, fitting selected points of interest to a curve, or interpolating from among raw data points. The identified points of interest can be selectively matched to the second image with an algorithm that can respond to the local characteristics of the image, such that robustness and accuracy of the matching are optimized.

The selective matching of the identified points of interest as described herein can use a combination of course to fine matching, feature based matching, and interpolation to provide both robustness and accuracy.

Robustness in matching is achieved by selectively matching the selectively identified points of interest in accordance with a course to fine matching strategy. The coarse-to-fine matching strategy can be based on normalized cross correlation and may employ a Gaussian pyramid. While at the coarse resolution image matching is robust, such that even poorly defined sparse images with little texture can be matched.

Accurate matching can be achieved by automatically going to the finest resolution for matching with an acceptable confidence score and directly matching the selected points for regions with acceptable confidence scores. For example, the confidence score may be based on normalized cross correlation, and regions of rich texture may be directly matched based on an acceptably high value of the normalized cross correlation coefficient. However, many of the identified points of interest may not be sufficiently matched based on region matching, such that additional matching can be used such as feature based matching and interpolation.

The coarse-to-fine correlation based matching can be combined with feature based matching for reliable matching result with good accuracy. For example, embodiments can follow a three step approach: (1) global offset estimation, e.g., through coarse-to-fine correlation on Laplacian pyramids that are less sensitive, in terms of lighting variation among images, than the original images, (2) matching of small regions surrounding the points that also output confidence scores, and (3) feature matching if the confidence score in step 2 is relatively low. The locations of points with extremely low matching scores can be interpolated from matched locations of other points with good matching scores. Constraints can be used such as soft epi-polar constraints, for example, which can be obtained with the first step of global offset estimation, for example without camera calibration. The additional constraints may also include a focus constraint, which can check or limit the matched point of interest so as to be in focus with the identified point of interest.

The selective robust matching described herein can be used for telestration that includes a system for both local and remote proctoring. The telestation system may comprise a friendly user interface (UI) for efficient interpretation of a surgeon's drawing and robust sparse point matching for efficiently generating reliable 3-D telestrated lines from two-dimensional (2-D) telestrated lines. The telestration system can display the raw video overlaid with telestrated lines that appear in 3-D to the system operator, for example, a resident surgeon.

Minimally Invasive Robotic Surgery

Figure 1B:
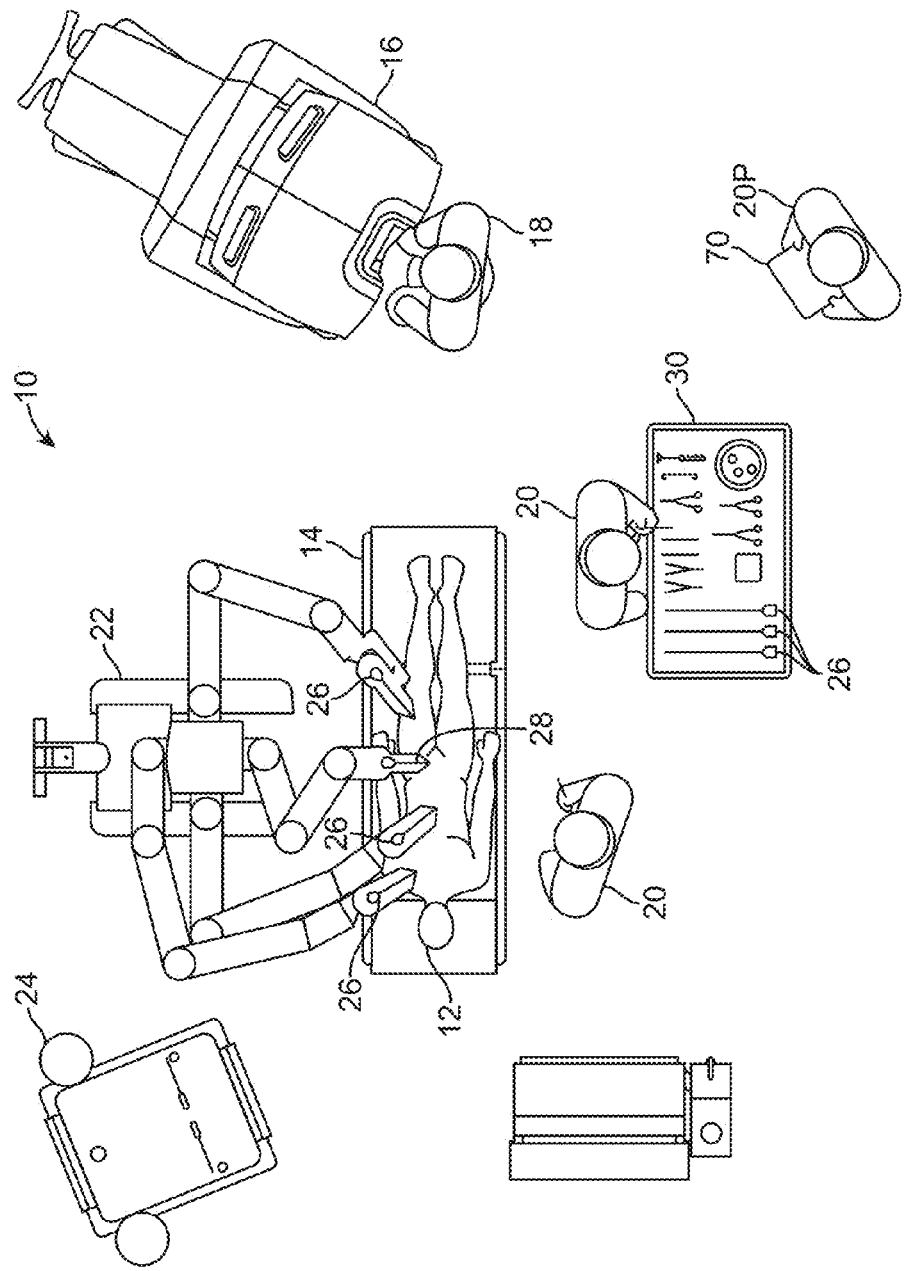

FIGS. 1A and 1B show a plan view illustration of a Minimally Invasive Robotic Surgical (MIRS) system 10, typically used for performing a minimally invasive diagnostic or surgical procedure on a patient 12 who is lying on an operating table 14. The system can include a surgeon's console 16 for use by a surgeon 18 during the procedure. One or more assistants 20 may also participate in the procedure. The MIRS system 10 can further include a patient side cart 22 (surgical robot), and a vision cart 24. The patient side cart 22 can manipulate at least one removably coupled instrument or tool assembly 26 (hereinafter simply referred to as a "tool") through a minimally invasive incision in the body of the patient 12 while the surgeon 18 views the surgical site through the console 16. An image of the surgical site can be obtained by an endoscope 28, such as a stereoscopic endoscope, which can be manipulated by the patient side cart 22 so as to orient the endoscope 28. The vision cart 24 can be used to process the images of the surgical site for subsequent display to the surgeon 18 through the surgeon's console 16. The number of surgical tools 26 used at one time will generally depend on the diagnostic or surgical procedure and the space constraints within the operating room among other factors. If it is necessary to change one or more of the tools 26 being used during a procedure, an assistant 20 may remove the tool 26 no longer being used at the time from the patient side cart 22, and replace it with another tool 26 from a tray 30 in the operating room. The MIRS system may comprise components of the da Vinci® Surgical System, commercially available from Intuitive Surgical, Inc. of Sunnyvale, Calif.

An instructor, for example a proctor surgeon 20P, may be present to observe and/or teach operator surgeon 18. Proctor surgeon 20P may view a display 70. Display 70 can be coupled to endoscope 28 in many ways to receive images from the endoscope, such that images of the surgical site, for example real time images, are shown on display 70. For example, display 70 may show images of the surgical site from one side (i.e., left or right side image) of the stereoscopic endoscope to proctor surgeon 20P. Although the proctor surgeon may often use a 2-D display, the proctor surgeon may have a 3-D display to view the telestration as seen by the operator surgeon.

Display 70 can be used for telestration such that proctor surgeon 20P can teach operator surgeon 18. Although proctor surgeon 20P is shown in the same room as operator surgeon 18, proctor surgeon 20P can be located remotely from operator surgeon 18. Display 70 may comprise a touch screen display, such that proctor surgeon 20P can draw illustrations, for example lines, on the display 70 by touching the display. The illustrations drawn on display 70 can be displayed to operator surgeon 18, so that proctor surgeon 20P can teach operator surgeon 18. Stereo and 3-D telestration for robotic surgery are described, for example, in U.S. Pat. App. Pubs. No. US 2007/0156017 A1 (filed Dec. 30, 2005) and US 2007/0167702 A1 (filed Dec. 30, 2005), the full disclosures of which are incorporated herein by reference.

Figure 1C:
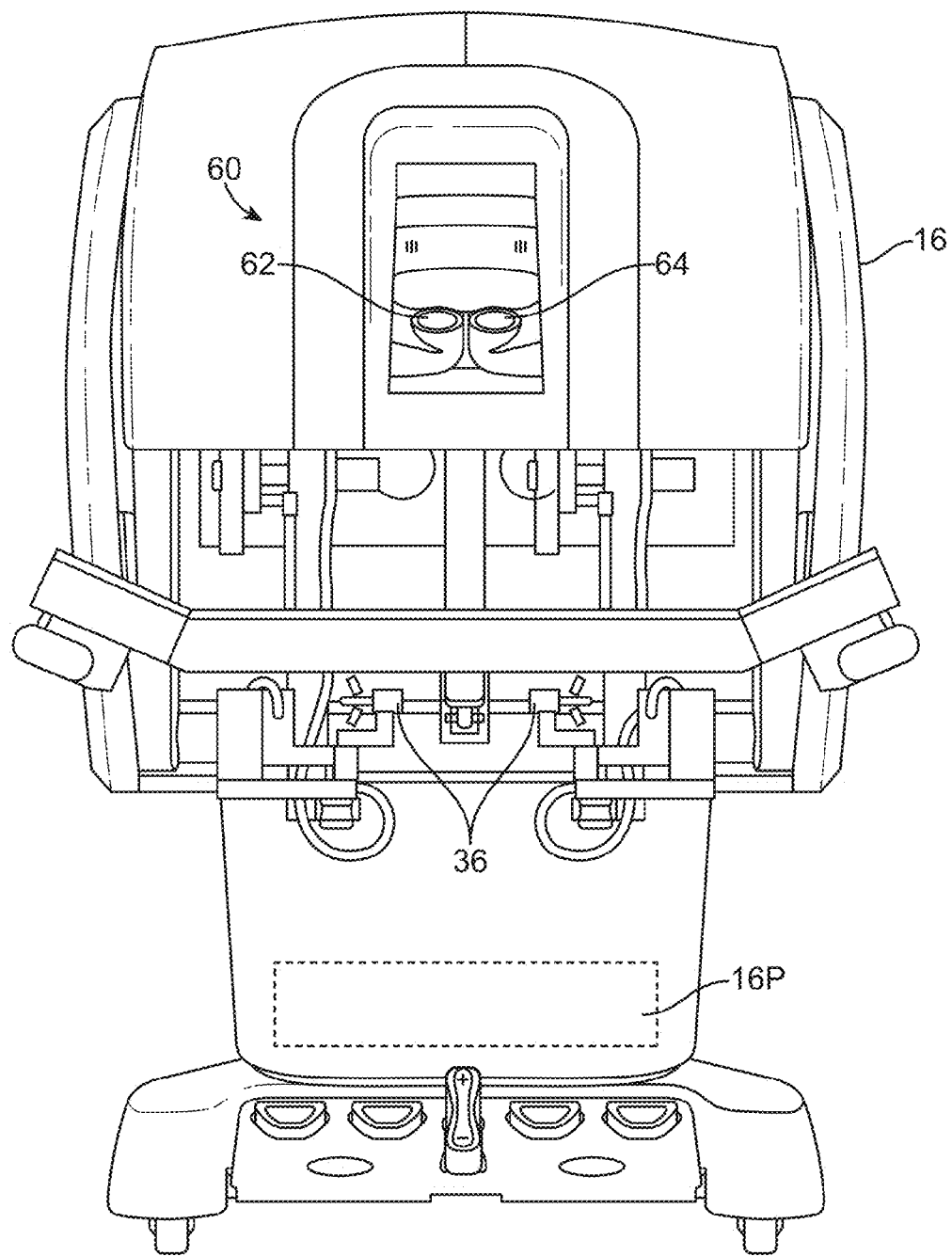
FIG. 1C is a front view of an operator surgeon's control console for a robotic surgery system, in accordance with embodiments.

FIG. 1C shows a front view of the operator surgeon's console 16. The operator surgeon's console 16 includes a display 60 comprising a left eye display 62 and a right eye display 64 for presenting the operator surgeon 18 with a coordinated stereo view of the surgical site that enables depth perception. The console 16 further includes one or more control devices 36 (masters), which in turn cause the patient side cart 22 to manipulate one or more tools (slaves). In some instances, control devices 36 will provide the same degrees of freedom as their associated tools 26 so as to provide the operator surgeon with telepresence, or the perception that the control devices 36 are integral with the tools 26 so that the operator surgeon has a strong sense of directly controlling the tools 26. To this end, position, force, and tactile feedback sensors may be employed to transmit position, force, and tactile sensations from the tools 26 back to the operator surgeon's hands through the control devices 36.

The processor system can be coupled to the first control devices 36 such that the control devices comprise a user input device, so that the user can control the telestration marks shown on the display. The first user input device may comprise a camera clutch pedal 36P coupled to the processor system such that the user can adjust a camera of the source of the pair of stereo images. For example, the telestration marks drawn by the proctor surgeon may be erased in response to the operator surgeon touching the camera clutch pedal, for example a resident surgeon touching the camera clutch pedal.

The operator surgeon's console 16 is usually located in the same room as the patient so that the operator surgeon may directly monitor the procedure, be physically present if necessary, and speak to an assistant directly rather than over the telephone or other communication medium. However, it will be understood that the operator surgeon can be located in a different room, a different building, or other remote location from the patient, allowing for remote surgical procedures. Therefore, the operator surgeon can be provided with a 3-D view of the surgical site at the remote location, for example provided with 3-D telestration at the remote surgical site.

Figure 1D:
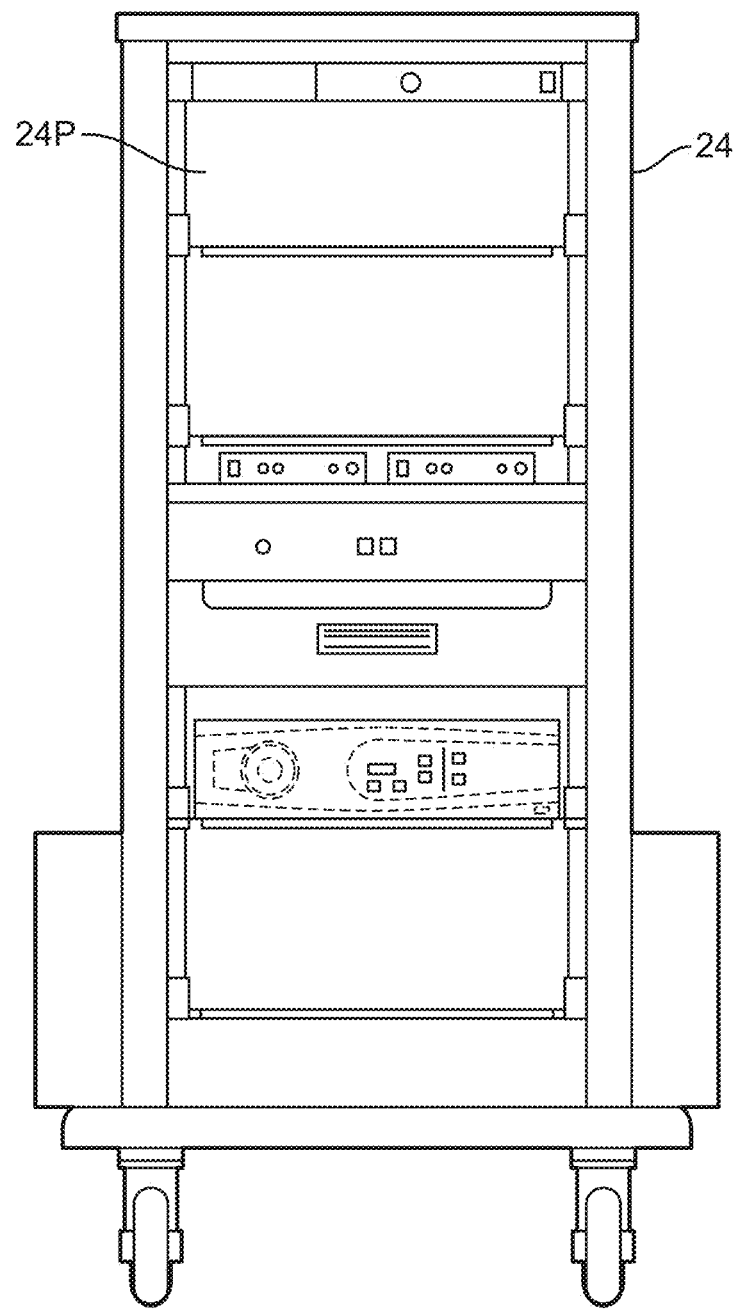
FIG. 1D is a front view of a robotic surgery system vision cart, in accordance with embodiments.

FIG. 1D is a front view of a vision cart 24. Vision cart 24 can be coupled with the endoscope 28 and can include a processor 24P to process captured images for subsequent display, such as to the operator surgeon on the operator surgeon's console, or on any other suitable display located locally and/or remotely. For example, where a stereoscopic endoscope is used, the vision cart 24 can process the captured images so as to present the operator surgeon with coordinated stereo images of the surgical site in 3-D. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations. Exemplary details of some of the possible image processing that can used are described in numerous patents and patent applications assigned to Intuitive Surgical, Inc., including, for example, U.S. Pat. No. 7,277,120 (filed Mar. 7, 2004), the full disclosure of which is incorporated herein by reference.

Figure 1E:
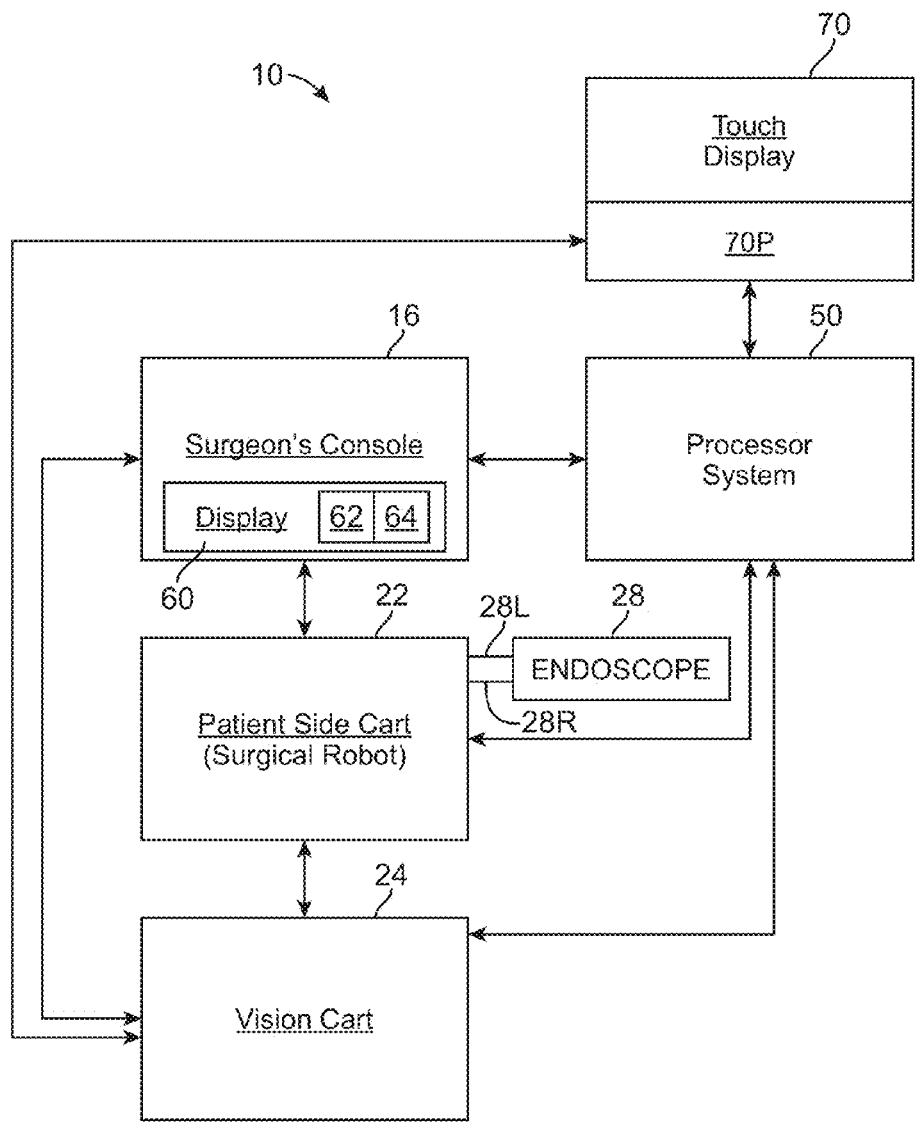
FIG. 1E diagrammatically illustrates a robotic surgery system, in accordance with embodiments.

FIG. 1E diagrammatically illustrates a robotic surgery system 10, showing communication paths between components. As discussed above, operator surgeon's console 16 can be used by the operator surgeon to control patient side cart 22 during a minimally invasive procedure. The patient side cart can use an imaging device, such as a stereoscopic endoscope 28, to capture images of the procedure site. Stereoscopic endoscope 28 comprises left output image 28L and right output image 28R that can be transmitted to vision cart 24, for example via cables included in patient side cart 22. As discussed above, the vision cart can process the captured images in a variety of ways prior to any subsequent display. Alternatively, or in combination, the patient side cart can output the captured images for processing outside the vision cart. For example, the patient side cart can output the captured images to a processor system 50, which can be used to process the captured images. A processor system 50 may comprise at least one of a processor located at vision cart 24, a processor located at patient side cart 22, a processor located at operator surgeon's console 16, and a processor 70P located at display 70. For example display 70 may comprise a tablet PC with a touch screen. The images can also be processed by a combination the vision cart and the processor system 50, which can be coupled together so as to process the captured images jointly, sequentially, and/or combinations thereof. One or more separate displays, for example display 60, can also be coupled with the processor system 50 and/or the vision cart for local and/or remote display of images, such as images of the procedure site or any other related images.

The displays coupled to system 10 may comprise additional displays and input devices, for example a third user display and a third user input device configured to receive input from a third user, so that the third user can draw telestration marks on the third user display. The second display and the second input device can be positioned local to the first user, for example in the same building. The third display and the third input device may be positioned remote to the first user, for example in a separate building. Additional 3-D displays can also be provided to system users, for example commercially available head mounted 3-D displays.

Selective Robust Sparse Image Matching for Robotic Surgery

The selective robust sparse image matching described herein can be applied to many applications. For example, the selective robust sparse image matching can be used to match points of interest spatially, such as to match points of interest from a left video frame to a right video frame. Such matching may occur with telestration in which a proctor surgeon, as described above, identifies points of interest for a first image, and the identified points are then located in a second image and shown in 3-D on the display to a trainee operator surgeon. The robust sparse image matching described herein can also be used match points of interest temporally, such as to match points of interest in sequential images from the same camera for tissue tracking in real time. Further, the image matching may also be useful for topography to determine surface shapes during surgery, to determine positions of markers in 3-D (for example, markers on tools to determine the tool location in 3-D), and also to determine positions of specific tissues. For example tumor tissue can be tagged with fluorescent markers, and the size, shape, and location of the tumor can be determined in 3-D in response to fluorescence of the markers. The tumor can then be shown on the display after the fluorescence stops, for example by tracking the tissue and identifying the regions of the images shown on the display that correspond to the tumor, for example with at least one of artificial lighting, highlighting, coloring, or marking, as described in U.S. patent application Ser. No. 12/164,363 (filed Jun. 30, 2008); Ser. No. 12/164,976 (filed Jun. 30, 2008); Ser. No. 12/165,194 (filed Jun. 30, 2008); Ser. No. 12/165,121 (filed Jun. 30, 2008); and Ser. No. 12/165,189 (filed Jun. 30, 2008), the full disclosures of which are incorporated herein by reference. The robust sparse image matching described herein can also be used to track sparse tissue points and display virtual markers positioned on tissue images in response to the tracked tissue points, in which the virtual markers can be used by surgeons for image guided surgery, for example as described in U.S. patent application Ser. No. 11/865,014 (filed Sep. 30, 2007); Ser. No. 11/865,015 (filed Sep. 30, 2007); and Ser. No. 11/865,016 (filed Sep. 30, 2007), the full disclosures of which are incorporated herein by reference. Surgeons may also use ultrasound for marking surgical margins, which margins can be tracked, for example, spatially or temporally.

Figure 1F:
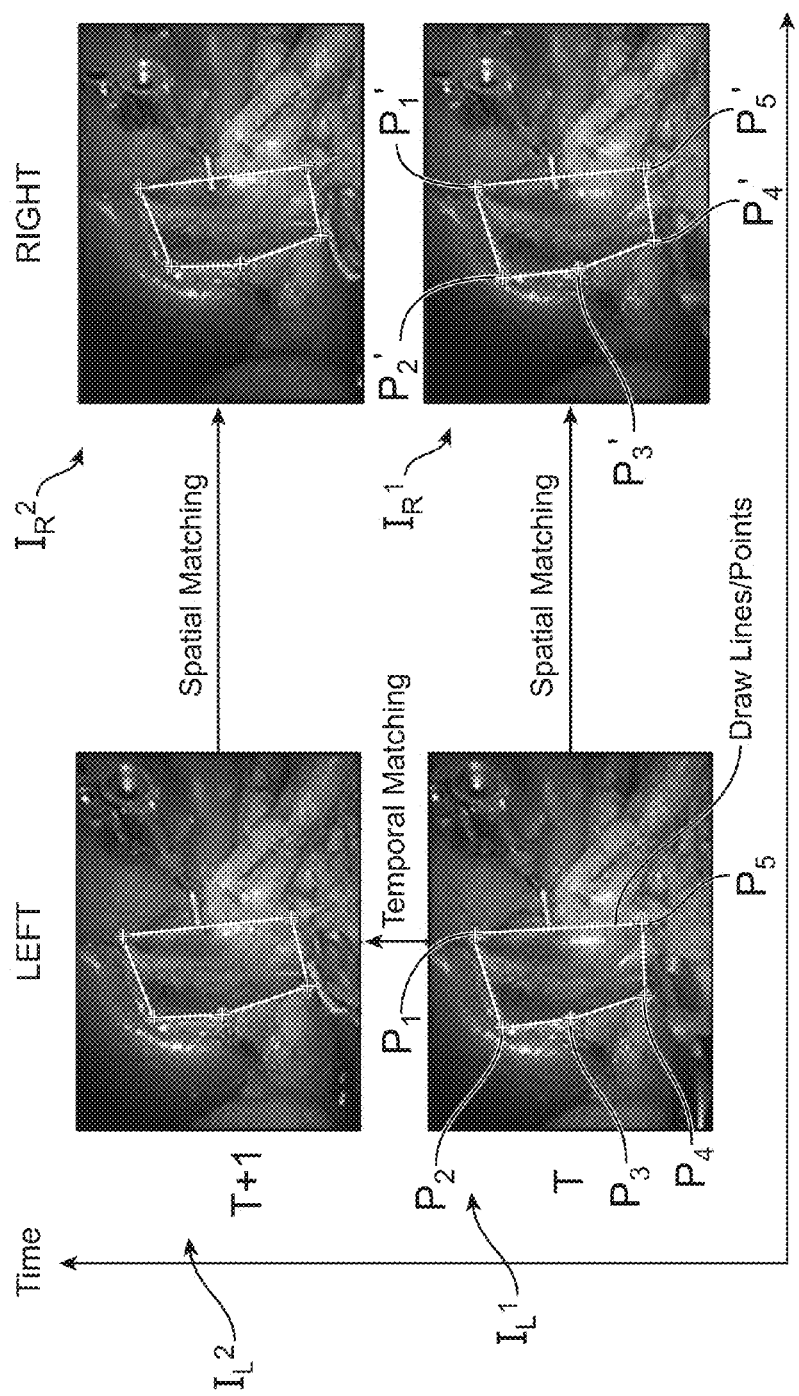
FIG. 1F shows left and right image series suitable for matching, in accordance with embodiments.

FIG. 1F shows examples of a left time series of images and a right time series of images suitable for matching. Such images can be present with telestration, for example. The left series comprises at least a first left image $I_L^1$ at time T and a second left image $I_L^2$ at time T+1. The right series comprises a first right image $I_R^1$ at time T and a second right image $I_R^2$ at time T+1. The right and left series of images as shown are illustrative of time series images captured at the same time from left and right sides of a stereoscopic surgical endoscope.

Robust image matching applications can be illustrated using the exemplary images shown in FIG. 1F. The selective image matching can be applied spatially, for example to left and right image pairs. The selective image matching can also be applied temporally, for example to match sequential images from the same side with temporal matching. Spatial matching can be used for 3-D telestration. Temporal matching can be used for tissue tracking. Spatial matching and temporal matching can be combined, for example to track tissue and move 3-D telestration lines in real time.

Points of interest can be identified in one or more images. Each of the points of interest can be identified in many ways as described above, for example with telestration. The locations of these points of interest in the first image are determined in the first image and the points of interest can be matched to other images, for example a second image. Five exemplary points of interest $P_1$, $P_2$, $P_3$, $P_4$, $P_5$ are shown in first left image $I_L^1$ at time T. The points of interest $P_1$-$P_5$ are shown connected by a line, which is representative of a telestration line that has been input and overlaid on the tissue image.

Once the points of interest have been identified in the first image, the points of interest in the first image are matched to a second image. Each of first point of interest $P_1$, second point of interest $P_2$, third point of interest $P_3$, fourth point of interest $P_4$, and fifth point of interest $P_5$ are matched to the first right image $I_R^1$ at time T, and each is shown as first matched point of interest $P'_1$, second matched point of interest $P'_2$, third matched point of interest $P'_3$, fourth matched point of interest $P'_4$, and fifth matched point of interest $P'_5$. Each of the matched points of interest are shown connected by a line.

Robust Sparse Image Matching Algorithm

The framework for the selective robust matching is illustrated in the following figures. At least three matching methods can be selectively combined: (i) coarse-to-fine global offset, (ii) coarse-to-fine region matching based on normalized cross correlation, and (iii) point matching based on feature detection and matching. The locations of points with an extremely low matching score can be inferred from matched locations of other good points. In addition, other constraints, such as soft epi-polar constraints, for example without camera calibration, can be added with the first step of global offset estimation. The locations of points of interest with extremely low confidence scores can be interpolated from the locations of other points of interest that have been matched with good confidence scores.

Figure 2A:
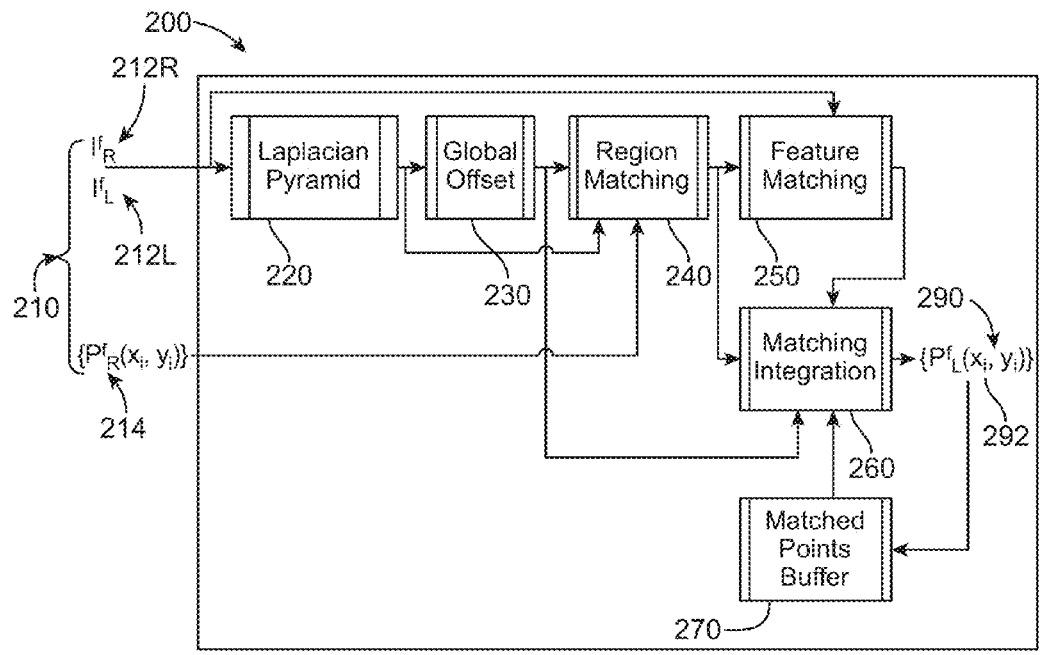
FIG. 2A shows a method of robust sparse image matching, in accordance with embodiments.

FIG. 2A shows a method 200 of selective robust sparse image matching. Method 200 can be implemented with a processor system as described above. The image matching components that can be used to selectively match the points of interest include a Laplacian pyramid 220, a global offset 230, feature matching 250, matching integration 260, and matched points buffer 270. An input 210 comprises left image series 212L, right image series 212R, and identified points of interest 214. Left image series 212L may comprise an array $V_L^f$. Right image series 212R may comprise an array $V_R^f$. Identified points of interest 214 may comprise an array of identified points $\{P_R^f(x_{if}, y_{if})\}$. Laplacian pyramid 220 is determined for the left and right image series. Global offset 230 is determined with Laplacian pyramid 220 as input. Region matching 240 is determined with identified points of interest 214, Laplacian pyramid 220, and global offset 230 as input. Feature matching 250 is determined with at least region matching 240 as input. Matching integration 260 is determined with global offset 230, region matching 240, and feature matching 250 as input. An output 290 comprises an array of matched points of interest 292. Matched points of interest 292 can be input into a matched points buffer 270 where the matched points are stored. Output 290 may also comprise a confidence score for each matched point.

Figure 2B:
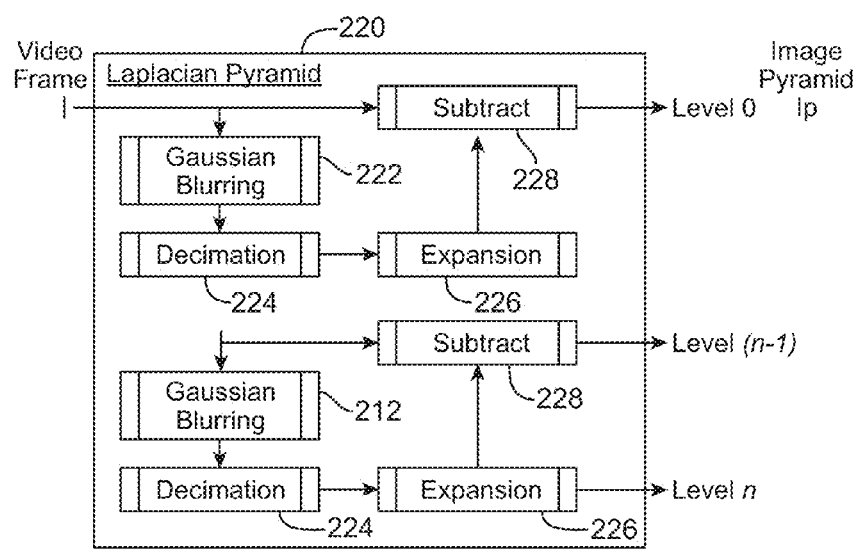
FIG. 2B shows a Laplacian pyramid as in FIG. 2A.

FIG. 2B shows Laplacian pyramid 220 as in FIG. 2A. Laplacian pyramid 220 can be constructed from each of the left and right images and may comprise known methods of determining a Laplacian pyramid. A video frame I is input. Gaussian blurring 222 blurs the input image. Decimation 224 reduces the size of the image. Expansion 226 expands the image. Subtraction 228 subtracts the original image from the processed image to obtain the Level 0 image of the Laplacian pyramid. Subsequent levels of the Laplacian pyramid are constructed until Level n of the pyramid is constructed.

FIG. 2C shows global offset 230 as in FIG. 2A. Global offset 230 can be calculated for levels of Laplacian pyramid 220. A right input 232 may comprise the Laplacian pyramid for the right image, and a left input 234 may comprise the Laplacian pyramid. Normalized cross correlation can be used to compare the left and right Laplacian pyramids to determine the output global offset 238. Output global offset 238 may comprise an offset of the left image 212L relative to the right image 212R.

FIG. 2D1 shows region matching 240 as in FIG. 2A. Input to region matching 240 comprises global offset 238, right image 232, left image 234, and points of interest 214, for example one point of interest from the array. Region matching 240 may comprise determining a region around the point of interest, such that the region is determined in response to the location of the identified point of interest. The input can be used to determine a pyramid region 242. For example, pyramid region 242 can be determined in response to the global offset and the identified point of interest. Normalized cross correlation 244 is used to determine the location of regions and can be repeated for the levels of the pyramid. Level determination 246 determines the optimal level L of the pyramid region. Output from region matching 240 comprises a region offset 248A and a confidence score 248B. Region offset 248A may comprise the location of the matched point based on region matching 240. The region offset can be used to determine the location of the point of interest, for example when the optimal level L and confidence score are appropriate.

The region matching can be performed in many ways. For example the regions of the first image can be matched to the second image with at least one of cross correlation, two-way matching, least squares regression, or non-linear regression. The region of the first image can be matched with a region of the second image, in which the region of the second image may be determined in response to the global image offset and the location of the point of interest of the first image. The cross correlation of the region first image with the region of the second image can be measured so as to obtain a correlation surface. The correlation surface comprises a maximum value, for example a normalized maximum value, that will often correspond to the matched point of interest. However, in some instances the correlation surface may comprise a multimodal correlation surface that includes multiple maxima, and the robust image matching algorithm can use additional criteria, for example focus and soft epi-polar constraints, to determine which one of the maxima corresponds to the matched point of interest of the second image.

The confidence score for region matching may be determined in many ways. The confidence score may comprise known measures of the quality with which the region of the first image is matched to the second image. For example, the confidence score may comprise at least one measure of goodness of fit, such as an $R^2$ value based on local linear regression of one-way matching results, i.e., pixel offsets from neighboring points. Confidence score can also be obtained through two-way matching. That is, given one interest point ($P_L$), in the left image, one can first find the matched point ($P_R$) on the right image. One can then find for $P_R$, the matched point $P_{R-L}$ in the left image. The confidence score is based on the distance between points $P_L$ and $P_{R-L}$. When cross correlation is used for matching, one can determine the confidence score based on a Gaussian fit of the correlation surface. In general, sharper Gaussian surface suggests higher confident score. In many instances when the surface is not smooth and contains multiple local maxima, one may first find these local maxima corresponding to the matched point of interest and then fit them to a Gaussian function.

FIG. 2D2 shows level determination 246 as in FIG. 2A and FIG. 2D1. A correlation surface from the normalized cross correlation 244 is input, and statistical analysis 246SA determines the optimal level L for the region matching based on, for example, matching score and corresponding confidence score. The region matching with automatic level determination can provide a good balance of accuracy and robustness.

As the points of interest can be sparse, feature matching 250 and interpolation may also be used to determine the locations of the matched points of interest.

Figure 2E:
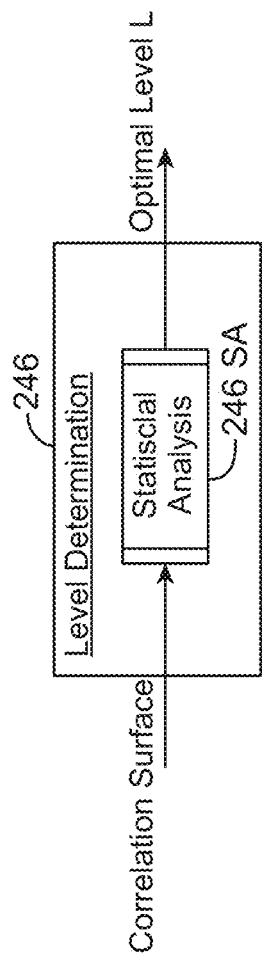
FIG. 2E shows feature matching as in FIG. 2A.
Figure 2E:
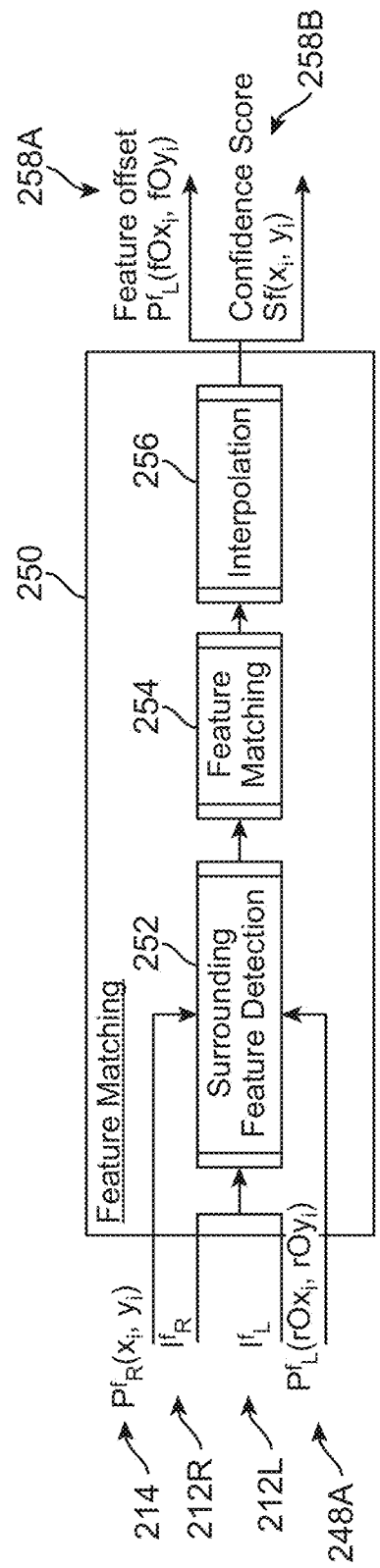

FIG. 2E shows feature matching 250 and interpolation as in FIG. 2A. Input to feature matching may comprise point of interest 214, right image 212R, left image 212L, and region offset 248A. Output of feature matching 250 may comprise a feature offset 258A and a feature confidence score 258B. A surrounding feature detection 252 can detect surrounding features. The point of interest 214 may comprise a feature that can be used for feature matching. A feature matching 254 matches the surrounding features and may also map a feature of the point of interest. An interpolation 256 can interpolate the location of the point of interest in response to the locations of the matched features. The location of the matched point of interest based on feature matching 250 may comprise a region offset 258A. A feature confidence score 258B can indicate the confidence of matched point of interest based on feature matching 250. In some embodiments, the feature match confidence score may comprise a binary score of "0" for unsuccessful matching (i.e., successful matching false) and "1" for successful matching (i.e., successful matching true).

The features of the first image can be matched with the second image in many ways. For example, the features of the first image can be matched to the second image with at least one of Harris corner detection, scale-space extrema detection, local extrema detection, or scale invariant feature transform. A known scale invariant feature transform is described in "Distinctive Image Features from Scale-Invariant Keypoints", authored by David Lowe and published in the International Journal of Computer Vision, 2004.

The confidence score for feature matching may comprise known confidence measures for feature matching such as a probability density function, a ratio of a distance from closest neighbor to a distance of a second closest neighbor, or a best bin first search. The confidence score can be determined as described in the Lowe publication.

FIG. 2E1 shows identified point of interest $P_1$ as in FIG. 1F for region and feature matching as in FIGS. 2D1, 2D2, and 2E. The region comprising a portion of the image determined in response to the identified point of interest. The identified point of interest may be contained with the portion of the image used for region matching. The portion of the image may comprise M by N pixels of the image. Although an 8 by 8 region is shown, the region may comprise many pixel sizes, for example 32 by 32 pixels, and 64 by 64 pixels. The image may comprise many known image formats and pixel sizes such as 1960 by 1080 pixels (1080P), 1024 by 768 pixels, 640 by 480 pixels, and 320 by 240 pixels. For each pixel of the image, an intensity gradient can be determined in response to the gray levels of the neighboring pixels. The gradients are shown as arrows.

FIG. 2E2 shows a feature comprising a keypoint descriptor for the region as in FIG. 2E1. The descriptor may comprise histograms of the intensity gradients of the image for sub-regions of the M by N region. For example, the M by N region can be divided into sub-regions, for example four sub-regions. For each sub-region a vector histogram can be obtained. The vector histogram may comprise cumulative vector intensities at angles as shown. The descriptors can be used to match point $P_1$ to determine the corresponding matched point in the second image.

FIG. 2F shows matching integration 260, as in FIG. 2A. The matching integration can make the final decision as to the location of the matched point in many ways. Input to matching integration 260 comprises confidence score 248B for region matching 240, region offset 248A for region matching, feature offset 258A for feature matching 250, global offset 238 for global offset 230, matched points of interest 292 from an array of matched points of interest, and confidence scores 292S for each of the matched points in the array of matched points. Output from matching integration 260 may comprise the location of the matched point of interest 292 and the confidences score 292S for the matched point of interest.

Several logic steps can be performed to determine which of region matching 240, feature matching 250, or geometry interpolation 266 is used to determine the location of the matched point of interest. Logic step 262 determines when confidence score 248B for region matching is above a threshold T1. When confidence score 248B is above threshold T1, a logic step 262A allows region offset 248A of the matched point to determine the location of the matched point of interest. Threshold T1 is set sufficiently high so as to ensure that region matching is used when the confidence score for region matching is high. When confidence score 248B is below threshold T1, a logic step 264 determines if region matching score is above a second threshold T2. If region matching confidence score 248B is greater than second threshold T2, a logic step 264A allows feature offset 258A to determine the location of the matched point. In some embodiments, logic step 264 comprises a comparison of the confidence score 258B for the feature matching to the second threshold T2. When confidence score 258B is above threshold T2, logic step 264A allows feature offset 258A to determine the location of the matched point of interest.

Geometry interpolation 266 of matched points of interest 292, for example matched points from the array of matched points, can be used to determine the location of the matched point 292, for example when at least one of region confidence score 248B or the feature confidence score 258B is below the respective threshold values. For example, a logic step 266A can allow geometry interpolation 266 when region matching score 248B is below second threshold T2. Also, as noted above, logic step 264 may comprise a comparison of feature confidence score 258B for feature matching 250 to threshold T2, such that interpolation 266 determines the location of matched point of interest 292 when region confidence score 248B is below first threshold T1 and feature confidence score 258B is below second threshold T2.

Geometry interpolation 266 may comprise an array of matched points of interest 292 and confidence scores 292S for each of the matched points of interest, and the array of matched points and confidence scores can be used to interpolate the location of the matched point of interest.

In some images interpolation may not be used to determine the location of the identified point of interest when the confidence scores for region matching and feature matching are low. For example, there may not be sufficient neighboring points of interest with corresponding matched points of interest that can be used for interpolation. The global offset 238 can be used to determine the matched point of interest for the identified point of interest with the low region matching score, low feature matching score, and insufficient neighboring points of interest with corresponding matched points of interest for interpolation.

A constraint check 268 can be used to determine the validity of the location of matched point of interest. The constraint check may also be used to improve the search, for example by limiting the search window based on the constraint and also by searching for an additional value when the matched point comprises a location outside the constraint. The constraint check may comprise at least one of a soft epi-polar constraint, a focus constraint, or a depth constraint.

With respect to the soft epi-polar constraint, the global offset can be used provide a soft vertical constraint between left eye and right eye images. For example the vertical constraint can be shifted vertically in response to a vertical offset of the global offset.

With respect to the focus constraint, sometimes points that are out of focus may not be suitable for matching. Also, one may not want to use out of focus points, even for those points with high confidence matching score, to determine the matching point for other points in the final step. The focus constraint may be implemented with two checks. The first check may comprise an absolute check in which it is determined if the disparity value between left and right images indicates an absolute out of focus condition for the matched point—that is, if the matched point is located outside of a normal operating range of the surgical system from the cameras. The second check comprises determining the local disparity value, which comprises a local displacement of the matched point of interest in addition to the global offset.

FIG. 2G shows a matched point buffer 270 for matched points of interest as in FIG. 2A. Inputs to matched point buffer 270 include matched point of interest 292 and confidence score 292S for the matched point of interest. The matched point of interest 292 is stored in a point buffer 272, and the confidence score is stored in a confidence score buffer. The matched points and scores stored in the buffer can be used to interpolate matched points of interest, as described above.

FIG. 2H shows interpolation 256 of features to determine the location of the point of interest as in FIG. 2A and FIG. 2E.

A point of interest P, for example point 292, comprises a location in the first image. Surrounding features $F_1$, $F_2$, and $F_3$ are determined with surrounding feature detection step 252, as described above. Surrounding features $F_1$, $F_2$, and $F_3$ are matched to the second image with feature matching step 254, as described above, to determine matched surrounding features $F'_1$, $F'_2$, and $F'_3$. The location of matched point P', for example matched point 292, can be determined based on the location of the matched surrounding features $F'_1$, $F'_2$, and $F'_3$. The following formula can be used for interpolation:

$$P' = \Sigma[F'k + (P - Fk)]/M \; k=1,\ldots,M$$

where P comprises the location of the point of interest in the first image and M comprises the number of features used for interpolation.

Figure 2I:
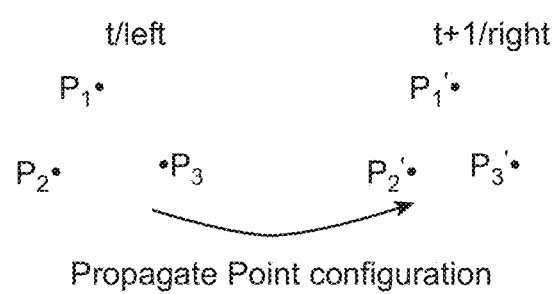
FIG. 2I shows interpolation of points of interest with previously determined points of interest as in FIG. 2A, FIG. 2F, and FIG. 2G.

FIG. 2I shows geometry interpolation 266 to determine locations of point of interest 292 with previously determined points of interest 292 as in FIG. 2A, FIG. 2F, and FIG. 2G. In 3-D telestration and other applications with a dynamic environment, selected points and/or lines may be occluded by other objects, such as the instrument tools. To handle the occlusion condition, one can utilize the concept of point configuration. Point configuration assumes that the geometric relationship of selected points should not change dramatically, for example with small tissue deformation. Based on this assumption, one can first detect bad matching based on confidence score from coarse-to-fine matching, as described above, and then invoke point configuration based matching. Point configuration matching allows interpolation, for example, to match an occluded point $P'_3$ based on the matching results of other points ($P'^{(i+1)}_k$). This interpolation can also be used with static images, in which the previously matched points of interest of an image can be used to infer the current point of interest of the image when the current point of interest does not have reliable matching.

The following is an example of geometry interpolation step 266 used in the matching integration step 260. The previously determined points of interest 292 can be stored in matched point buffer 270, as noted above. A point of interest $P_3$, for example point 292, comprises a location in the first image. Surrounding points of interest $P_1$ and $P_2$ can be identified, as described above. Surrounding points of interest $P_1$ and $P_2$ are matched to the second image with at least one of region matching step 240 feature matching step 250, as described above, to determine the location of matched points of interest $P'_1$ and $P'_2$. The location of matched point $P'_3$, for example matched point 292, can be determined based on the location of the surrounding matched points of interest $P'_1$ and $P'_2$. The following formula can be used for interpolation:

$$P_3'^{(i+1)} = \Sigma S_k * [P_k'^{(i+1)} + (P_k^t - P_3^t)] \; k=1,\ldots,N/3$$

where $S_k$ comprises the normalized confidence score, where $\Sigma S_k = 1$, and where N comprises the number of previously matched points of interest used for interpolation.

Robust Efficient 3-D Telestration for Local and Remote Robotic Proctoring

The above-described robust selective image matching can be used with telestration that is practical for surgeons to use. Since sparse image matching can be applied after the proctor surgeon's drawing, the 3-D telestration architecture is very efficient. The 3-D telestration architecture is suitable for both local 3-D and remote proctoring. In the case of remote proctoring, the matching may occur locally at the surgical site, and only the locations of drawn points and lines are communicated through a network between the sites.

Figure 3A:
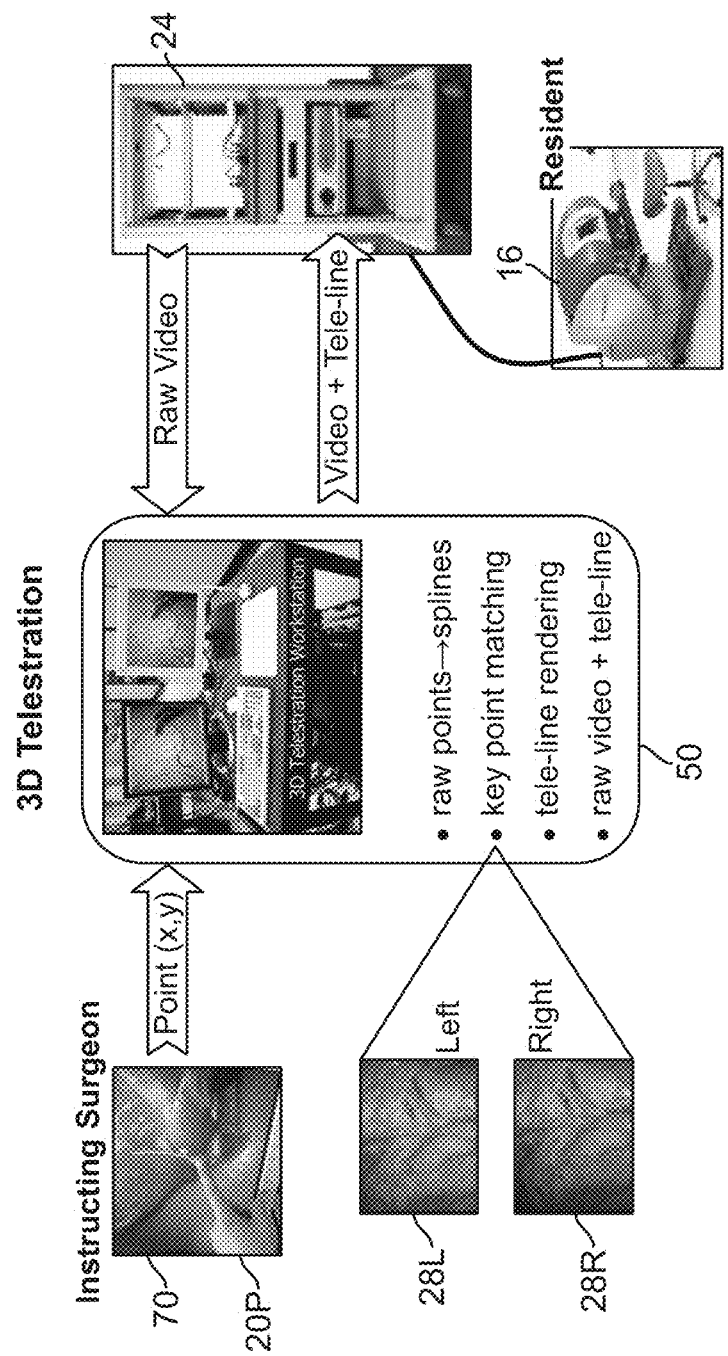
FIG. 3A shows 3-D telestration with a system as in FIGS. 1A to 1F.

FIG. 3A shows 3-D telestration with a system 10 as in FIGS. 1A to 1F. A stereoscopic endoscope, as described above, can acquire and output left image 28L and right image 28R, which may comprise a series of left and right images. The images from the endoscope are transmitted to the computer system 50, which may comprise a processor of vision cart 24 as noted above. The images from one side of the endoscope, for example left side image 28L, are transmitted to touch display 70, where the images are visible to the proctor surgeon 20P. Proctor surgeon 20P can then draw a line on the image to indicate points of interest. For example a line may comprise several points of interest. Although a touch screen display is shown, the points of interest can be identified in many ways with an input device, for example with at least one of a touch display, a touch screen display, a pointing device, a track pad, a mouse, a keyboard, a joystick, or voice commands.

Identified points of interest, for example points along a line, are transmitted from the touch display 70 to processor system 50. The processor system 50 can match the identified points of interest from the first image, for example a left image, to points in a second image, for example a right image. Although the points of interest can be matched in many ways, many embodiments use robust image matching, as described above, to match the points of interest from the first image to points in the second image. The first image may comprise a first series of images, and the second series may comprise a second series of images in which the points of interest identified from the first series are matched to the second series. The processor system 50 may fit the raw points to spline curves and display the spline curves to the proctor surgeon and the operator surgeon. The processor system 50 may perform telestration line rendering or raw video plus telestration line rendering.

Figure 3B:
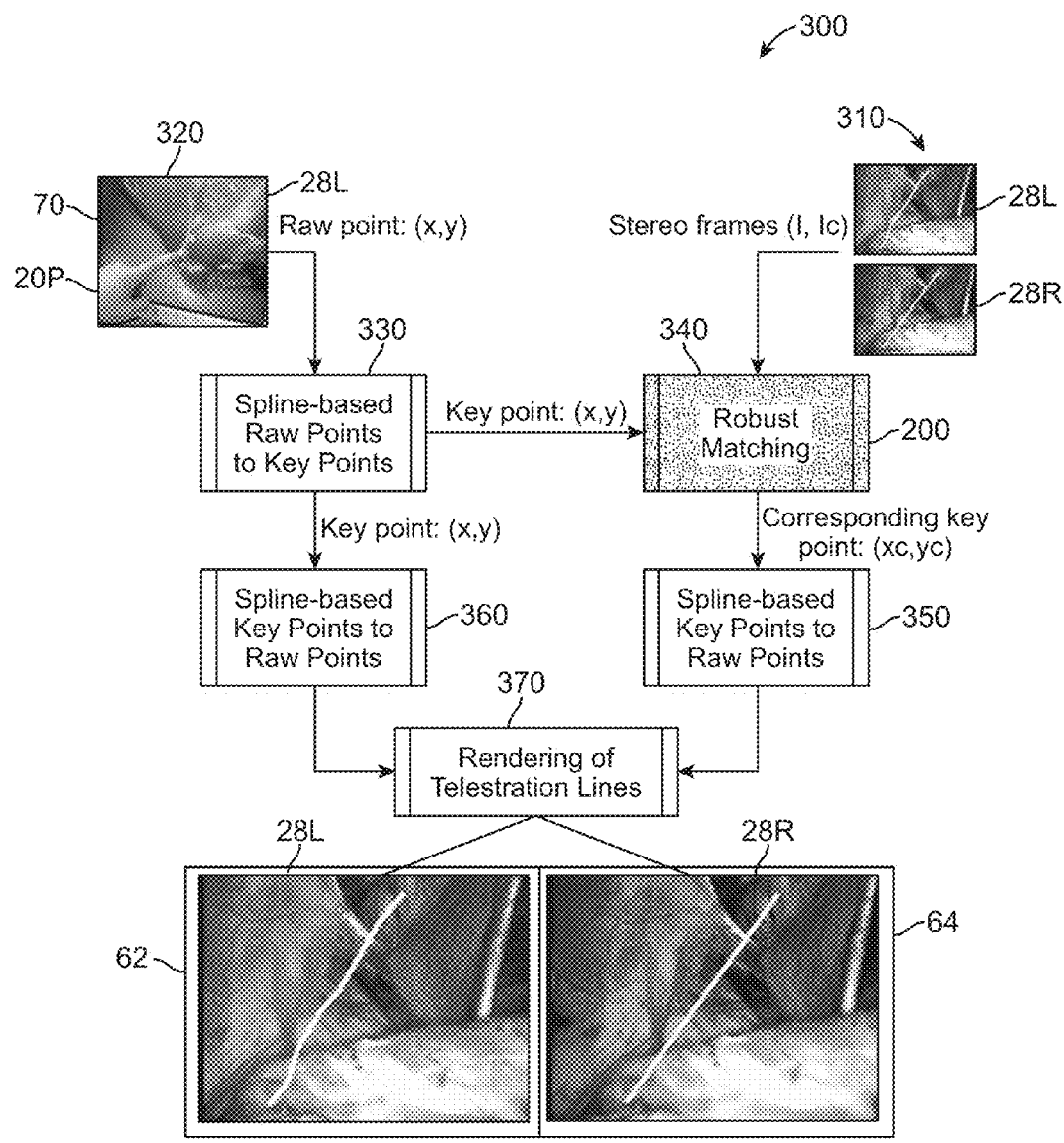
FIG. 3B shows a method of 3-D telestration with a system as in FIG. 3A and robust image matching as in FIGS. 2A to 2I.

FIG. 3B shows a method 300 of 3-D telestration with a system as illustrated in FIG. 3A and robust image matching as illustrated in FIGS. 2A to 2I. A step 310 acquires stereo image frames from the endoscope 28, as described above. The stereo frames comprise a left image 28L and a right image 28R. The left image may comprise a series of left images and the right image may comprise a series of right images, as noted above. A step 320 displays at least one of the left image 28L, or right eye 28R to the proctor surgeon 20P on touch display 70, as described above. The proctor surgeon can identify points of interest with his or her finger on the touch display, and may draw a line in real time on the touch display, in which points of interest can be stored in a buffer and shown on the display 70 after the points of interest are identified. The points output from the display may comprise raw points with coordinates indicating where proctor surgeon 20P touched display 70. A step 330 can fit the raw points to a spline to determine the key points.

The points of interest used for matching from the first image to the second image can be identified and determined in many ways, and the points of interest may comprise at least one of a raw point from the display or a key point determined in response to the raw points. The points of interest used for matching may comprise raw data points, such as raw data points from the display input device. Matching the raw points directly from the first image to the second image can decrease post-processing of the points, such that there may be no need to re-render telestration lines. This avoidance of re-rendering of telestration lines can be beneficial, because some surgeons may not like re-rendering of telestration lines in some instances.

Key points can be used to adjust the number of points used for matching in response to the characteristics of the image, the local matching results, and the optimal sampling density. For example, key points can be useful to reduce the number of points used for matching. For dynamic tissue tracking, decreasing the number of key points may decrease the matching time so as to increase the speed of the tracking. The key points can be determined in many ways. For example, key points can be determined with a spline fit of the raw points. A step 340 matches the points of interest from the first image to the second image, for example with method 200 of robust image matching, as described above. The matched points of interest may comprise corresponding key points, for example when key points from the left image 28L are matched to the right image 28R. A step 350 can convert the spline based matched key points to raw points for display to the operator surgeon on the right side display 64 of display 60. A step 360 can convert the spline based key points to raw points for display to the operator surgeon on the left display 62 of display 64. A step 370 renders the telestration lines and displays the telestration lines to the operator surgeon on display 60.

Key points can also be used to increase the number of points used for matching. The key points can be generated in response to at least one of the geometry of the drawn telestration line, the sampling intensity, or local matching result. For example, a proctor surgeon can draw a line very quickly, such that only a small number of raw points are drawn and input as raw data. These input raw data points can be converted into key points, and the number of key points may be just two, so as to represent a straight line. This number of key points may be insufficient, since the tissue underneath this drawn line may have a complicated surface. An increased number of key points can represent the tissue structure more accurately. Therefore, the number of key points can be increased in response to at least one of the complexity of the tissue surface, the number of key points, the density of key points along the telestration line, the number of input raw data points, or a density of input raw data points. For example, the distance between raw points can be calculated, and if that distance is too large, then key points can be automatically added in response to the distance between the raw points.

The spline-based raw points to key points conversion for matching, or key points to raw points conversion for displaying, is based on spline representation of the points. For example, more points may be needed in a high curvature area than in a low curvature area in order to mathematically represent the drawn line.

In some embodiments, the key points can be adjusted in response to local matching results, for example so as to constrain the number of key points in response to the complexity of the tissue structure. For example, if the underlying tissue structure is complicated, more key points can be used. However, in some instances this increase in key points may result in longer post-processing and the re-rendering of the telestration lines, and therefore selectively increasing the key points in response to the complexity of the tissue can minimize post-processing increases.

FIG. 3C shows a method 390 matching of points from a first series of images to a second series of images. Left output image 28L comprises a first series of left output images and right output image 28R comprises a second series of right output images. The first and second series of images may comprise real time digital images. The left side image comprises first left output image 28L1 at time T, second left output image 28L2 at T+1, and third left output image 28L3 at T+2. A step 392A acquires first left output image 28L1 corresponding to time T. The proctor surgeon 20P identifies a first point of interest $P_1$ on the image shown to the proctor surgeon, for example the first left output image 28L1. A step 392B matches point $P_1$ to the right side image 28R, for example first right output image 28R1 corresponding to time T so as to determine a first matched point of interest P'$_1$. A step 392C shows the first matched point of interest P'$_1$ on the first right image 28R1, and matched point of interest P'$_1$ can be shown on subsequent images. The first point of interest P$_1$ and first matched point of interest P'$_1$ can be stored in a buffer of points of interest and matched points.

A step 394A acquires a left output image 28L corresponding to time T+1, for example second left output image 28L2. The proctor surgeon 20P identifies a second point of interest P$_2$ on the image shown to the proctor surgeon, for example the second left output image 28L2. A step 394B matches point P$_2$ to the right side image 28R, for example second right output image 28R2 corresponding to time T+1 so as to determine a second matched point of interest P'$_2$. A step 394C shows the second matched point of interest P'$_2$ on the second right image 28R2, and the second matched point of interest P'$_2$ can be shown on subsequent images. The second point of interest P$_2$ and second matched point of interest P'$_2$ can be stored in the buffer of points of interest and matched points and used for display with subsequent images. For example, the first point of interest and second point of interest can be shown together on the left display 62 and the first matched point of interest and the second matched point of interest can be shown together on the right display 64, so as to present the points as 3D information to the resident. The points of interest can be connected with a first left line, and the matched points of interest can be connected with a second left line to show the telestration line to the user.

A step 396A acquires a left output image 28L corresponding to time T+2, for example third left output image 28L3. The proctor surgeon 20P identifies a third point of interest P$_3$ on the image shown to the proctor surgeon, for example the third left output image 28L3. A step 396B matches point P$_3$ to the right side image 28R, for example third right output image 28R3 corresponding to time T+2 so as to determine a third matched point of interest P'$_3$. A step 396C shows the third matched point of interest P'$_3$ on the third right image 28R3, and the third matched point of interest P'$_3$ can be shown on subsequent images. The third point of interest P$_3$ and third matched point of interest P'$_3$ can be stored in the buffer of points of interest and matched points and used for display with subsequent images. For example, the first point of interest, second point of interest, and third point of interest can be shown together on the left display 62, and the first matched point of interest, the second matched point of interest and the third matched point of interest can be shown together on the right display 64, so as to present the points as 3-D information to the resident. The points of interest can be connected with 3-D telestration lines, for example splines, as noted above.

When defined, the points of interest may be tracked in subsequent images with tissue tracking and the locations of the points adjusted in response to the tissue tracking. The defined array of points that are tracked in subsequent images may comprise the identified points of interest, the matched points of interest, or both. The tissue tracking may also be initiated when a single point of interest has been identified, for example initiated with a single point identified from first image of a series of images, and additional points added to the array and tracked as additional points of interest are identified from the series of images.

The 3-D telestration system can have many user interface features to enhance the visual experience of the user. For example, the stereo telestration can be optional. In some instances, telestration may be presented to the user in one eye only, for example when image matching is poor. The system may be configured to accommodate these situations where robust image matching may not be sufficient to match the points of interest. For example, a left/right eye selection toggle can provided for both the proctor surgeon's interface and the operator surgeon's console interface. This toggle may also be provided for an assistant to the operator surgeon who may also have a display for viewing. The assistant may have a display similar to the proctor surgeon, and alternatively or in combination may have a 3-D display, for example a head mounted 3-D display. This left/right eye selection can be global. When the left eye is selected and the proctor is viewing the left channel of the stereo pair, the telestration marks will be rendered on the operator surgeon's left eye, and vice-versa. For example, when the operator surgeon is left eye dominant and selects left eye telestration overlay, then the proctor surgeon's interface will display the left channel of the stereo pair. This global change ensures that the telestration is drawn by the proctor surgeon for the eye that is selected eye for viewing by the operator surgeon. As the left/right eye toggle can be provided for each of the proctor surgeon's interface, the assistant's interface and the operator surgeon's console interface, each of the operator surgeon, the proctor surgeon, and the assistant may select which one of the left or right images is shown to the proctor surgeon for telestration.

An erase button can be present, such that at least one of the proctor surgeon, the operator surgeon, or the assistant can overwrite or remove the telestration lines.

The 3-D telestration system may use an automatic decaying feature. For example, the telestrated lines may disappear after a certain amount of time, for example, 3 seconds, after drawing such that at least one of the proctor surgeon, the operator surgeon or the assistant does not have to press an erase button to remove the lines. This automatic line decay feature can be programmable to fit the different requirements various surgeons.

The 3-D telestration system may test for valid matching, such that telestration lines on the matched side are of high quality. For example, the telestration system may determine when to show the matched points and the matched telestration lines. The telestration line may be visible without matching on the side viewed by the proctor surgeon, and the telestration line may not appear on the matched side until the matching occurs with sufficient confidence over a region.

Figure 4B:
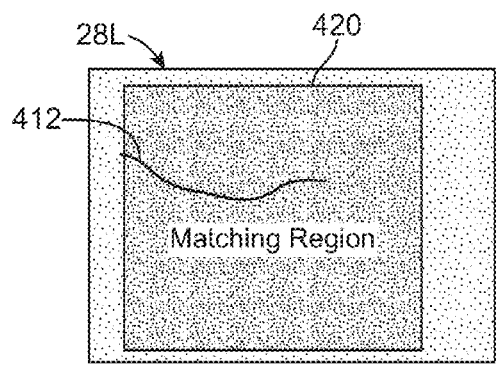
FIG. 4B shows the left image with matched points appearing only in the valid matching region, in accordance with embodiments.
Figure 4A:
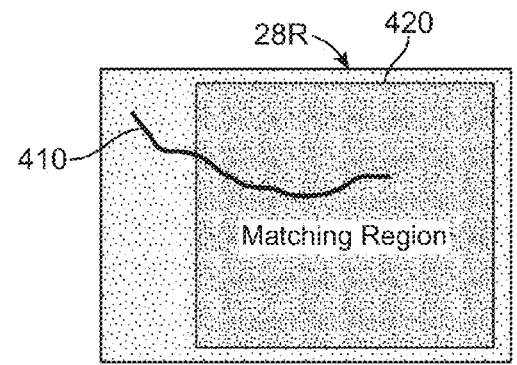
FIG. 4A shows a proctor surgeon's drawing on a right image without restriction, in accordance with embodiments.

FIG. 4A shows a proctor surgeon's drawing on a first selected side, for example a right image 28R, without restriction, such that the proctor surgeon can draw with full freedom. The drawing comprising a telestration line 410 is seen in the selected eye by the resident user. As noted above, the selected eye view for drawing without restriction may comprise either the right eye view or the left eye view, and the right eye view is shown as an example. The points of interest of the telestration line can be matched to the second side, for example a left side image 28L. Due to the stereoscopic vision feature, small areas visible in the right side image may not be seen in the left side image. Therefore, a point of interest in the image for one eye may not have a corresponding matching point in the image for the other eye. Therefore, the telestration system may determine a valid matching region 420, in which the validly matched points of interest and the telestration line can be shown. The valid matching region 420 may comprise a region where the first image can be matched to the second image within the physical constraints of the system, such as the endoscope optics and left and right image sensors. There can also be non-matching regions of the first image and non-matching regions of the second image outside the valid matching regions of the first and second images where it is not possible to match the first image with the second image.

FIG. 4B shows the left image with matched points appearing only in the valid matching region 420. The processor system can be configured to perform matching and show the matched drawing only when the proctor surgeon's drawing is within the valid matching region.

Although robust image matching as described herein can successfully match identified points of interest for telestration with substantial reliability, there can be some instances where the identified points of interest of the first image may not be matched to the second image. For example, with a stereo configuration of camera images, there can be some regions where it is not possible to match the first image with the second image due to the stereo view of the cameras. In non-matching regions of the first image where the proctor surgeon draws, the identified points of interest of the non-matching region of the first image cannot be matched with the second region, and in response the efficient 3-D telestration algorithm may not attempt to match the identified points of interest of the non-matching region of the first image with the second image. However, as the information provided by the proctor surgeon in the non-matching region may have some benefit, the portion of the telestration line drawn in the non-matching region of the first image may be shown on the operator surgeon's display with the first image for the operator surgeon to see the telestration line drawn by the proctor surgeon in the non-matching region. At least a portion of the telestration indicia may be shown in one eye only in additional situations, for example when the image matching comprises low confidence scores, such as when several neighboring matched points of interest have low confidence scores such that the points of interest cannot be interpolated. As the user interface as described herein provides great flexibility and allows each user to customize the interface, in some instances a user can turn off the 3-D telestration and view 2-D telestration, for example with global offset 230 or a predetermined offset, and may even view telestration with one eye only. Therefore, components and attributes of the above-described system can be beneficially combined in many ways that a person of ordinary skill in the art will recognize.

The 3-D telestration framework described above can be used for both static tissue tracking and dynamic tissue tracking, as described above. Dynamic tissue tracking can be based on initial static tissue tracking followed by dynamic tissue tracking. The proctor surgeon draws lines on a 2-D image, as described above. The 3-D telestration system determines locations of the lines and points of interest on the corresponding matched image, for example on a second side as described above. In response to motion of the tissues, for example blood vessels, the robust image tracking can put the telestrated lines on top of these moving tissues in real time. For example the telestrated lines may be shown to move across successive video frames in response to tissue movement, the lines remaining associated with the originally designated points of interest.

Experimental Testing

A 3-D telestration prototype has been implemented and demonstrated based on the da Vinci® Surgical System commercially available from Intuitive Surgical, Inc. of Sunnyvale, Calif. A proctor surgeon can draw arbitrary lines from an input device, such as a touch screen (e.g., a known Elo Touch Screen available from Elo TouchSystems) or a touch pad (e.g., a known BAMBOO touch pad commercially available from Wacom). A 3-D Telestration workstation has been built that carries out interpretation of the proctor surgeon's drawing. A robust matching algorithm, as described above, has been used to generate the lines on the other image (e.g., left eye view) that corresponds to the image (e.g., right eye view) where the proctor surgeon is drawing. The 3-D telestrated lines can be overlaid with both left eye and right eye views onto the operator surgeon console.

FIG. 5A shows a left image 510 with the proctor surgeon's drawing 512 comprising points of interest. A suture 514 is present (out of focus) in right image 510. Left image 510 is shown on the operator surgeon display and the proctor display.

FIG. 5B shows a right image 520 with the matched drawing 522 comprising the matched points of interest from FIG. 5A, in which the points of interest are matched without constraints. Suture 514 (out of focus) appears shifted slightly to the left in relation to the imaged tissue. The matched proctor surgeon's drawing 522 is distorted and appears located on the suture 514 instead of being located on the selected tissue as shown in FIG. 5A. Right image 520 can be shown on the display viewed by the operator surgeon.

FIG. 5C shows a right image 530 with matched points of interest from FIG. 5A, in which the matched drawing 532 comprising the matched points of interest are matched with soft epi-polar and focus constraints. Right image 530 can be shown on the operator surgeon display, such that proctor surgeon's drawing 512 and matched drawing 532 are shown in 3-D to the operator surgeon on the display, and hence it appears to follow tissue contours.

FIG. 5C shows that, as compared against image 520, the soft epi-polar and focus constraints can improve image matching and identification of the selected points of interest. The focus constraint can eliminate incorrectly matched points of interest, for example points of interest incorrectly matched to the suture, which is out of focus. One of ordinary skill in the art will recognize that the soft epi-polar constraint and the focus constraint can be applied in many ways, for example to eliminate bad points, and these constraints may also be used to improve the search area and identify the matched points of interest.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A medical system comprising:
an image capture device for capturing stereo images of a work site, each stereo image including a first two-dimensional image and a second two-dimensional image, wherein corresponding points in the first and second two-dimensional images depict a common point in the work site and exhibit a disparity between the corresponding points so as to indicate a depth of the common point relative to the image capture device;
a stereo display displaying the first and second two-dimensional images so as to provide a three-dimensional viewing experience; and
a processor that is programmed to: receive information of a first telestration indicative of user selected points of interest of the first two-dimensional image; selectively match the selected points of interest of the first two-dimensional image to corresponding points of the second two-dimensional image to determine matched points of interest of the second two-dimensional image by computing a plurality of image offsets wherein each of the plurality of image offsets is computed using a different image matching method than all others of the plurality of image offsets, and by using one of the computed plurality of image offsets which is selected according at least partially to one or more confidence scores of the plurality of image offsets, wherein the matched points of interest correspond to a second telestration mark; and cause the first and second telestration marks to be displayed respectively over the first and second two-dimensional images on the stereo display such that the first telestration mark and the second telestration mark appear as a single three-dimensional telestration mark on the stereo display.

2. The medical system of claim 1, further comprising:
a user interface that is usable by a first user to define the first telestration by indicating the user selected points of interest of the first two-dimensional image.

3. The medical system of claim 2, wherein the user interface includes a touchscreen display for displaying the first two-dimensional image.

4. The medical system of claim 2, wherein the user interface includes a monovision display and an input device, wherein the input device is usable by the first user to define the first telestration by indicating the user selected points of interest on the first two-dimensional image being displayed on the monovision display.

5. The medical system of claim 1, wherein the plurality of image offsets includes at least two of: a global offset which the processor is programmed to compute by using a coarse-to-fine global offset image matching method, a region offset which the processor is programmed to compute by using a coarse-to-fine region image matching method, and a feature offset which the processor is programmed to compute by using a point matching method based upon feature detection and matching.

6. The medical system of claim 5, wherein the processor is programmed to compute the global offset by using normalized cross correlations to compare information of the first and second two-dimensional images.

7. The medical system of claim 5, wherein the processor is programmed to compute the region offset by matching a region of the first two-dimensional image to a region of the second two-dimensional image by using at least one of cross-correlation, two-way matching, least squares regression, and non-linear regression.

8. The medical system of claim 5, wherein the processor is programmed to compute the feature offset by matching features of the first two-dimensional image to features of the second two-dimensional image by using at least one of Harris corner detection, scale-space extrema detection, local extrema detection, and scale invariant feature transform.

9. The medical system of claim 1, wherein the processor is programmed to perform the selectively matching by at least one of selectively matching regions, selectively matching features, selectively interpolating features, and selectively interpolating previously matched points of interest.

10. The medical system of claim 9, wherein the processor is programmed to determine region match confidence scores when the regions are selectively matched, determine feature match scores when the features are selectively matched, selectively match the features in response to the region match confidence scores, selectively interpolate the features in response to the feature match scores, and selectively interpolate the previously matched points of interest in response to the feature match scores; and wherein locations of the matched points of interest are determined by using the region match confidence scores and the feature match scores.

* * * * *